United States Patent [19]
Yukimasa et al.

[11] Patent Number: 6,110,909
[45] Date of Patent: Aug. 29, 2000

[54] BENZOXAZEPINE COMPOUNDS, THEIR PRODUCTION AND USE AS LIPID LOWERING AGENTS

[75] Inventors: Hidefumi Yukimasa, Nara; Yasuo Sugiyama, Kawanishi; Ryuichi Tozawa, Yokohama, all of Japan

[73] Assignee: Takeda Chemical Industries, Ltd., Osaka, Japan

[21] Appl. No.: 09/043,265

[22] PCT Filed: Sep. 12, 1996

[86] PCT No.: PCT/JP96/02596

§ 371 Date: Mar. 12, 1998

§ 102(e) Date: Mar. 12, 1998

[87] PCT Pub. No.: WO97/10224

PCT Pub. Date: Mar. 20, 1997

[30] Foreign Application Priority Data

Sep. 13, 1995 [JP] Japan .................................. 7-235457

[51] Int. Cl.[7] .......................... A61K 31/553; A61P 9/10; C07D 267/14; C07D 413/06; C07D 413/14
[52] U.S. Cl. ...................... 514/211.05; 540/490
[58] Field of Search ............................. 514/211; 540/490

[56] References Cited

U.S. PATENT DOCUMENTS 5,885,979  3/1999  Yukimasa et al. ...................... 514/183

FOREIGN PATENT DOCUMENTS

| 0 567 026 A1 | 4/1993 | European Pat. Off. . |
| 0 645 378 A1 | 9/1994 | European Pat. Off. . |
| 0 705 607 A2 | 9/1995 | European Pat. Off. . |
| 0645377 A1 | 9/1995 | European Pat. Off. . |
| 0 710 725 A1 | 10/1995 | European Pat. Off. . |
| WO 95/21834 | 8/1995 | WIPO . |

*Primary Examiner*—Mukund J. Shah
*Assistant Examiner*—Brenda Coleman
*Attorney, Agent, or Firm*—David G. Conlin; Jennifer K. Holmes; Dike, Bronstein, Roberts & Cushman, LLP

[57] ABSTRACT

This invention provides new benzoxazepine compounds represented by the formula:

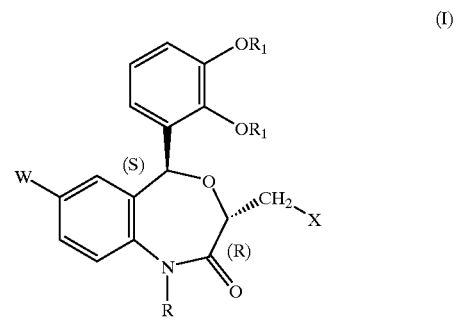

[wherein R stands for a lower alkyl group optionally substituted with a hydroxyl group, X stands for an optionally substituted carbamoyl group or an optionally substituted heterocyclic group having a deprotonatable hydrogen atom, $R_1$ stands for a lower alkyl group and W stands for a halogen atom] having activities of lowering chlesterol-level and lowering trigluceride-level, and being useful for prophylaxis and therapy of hyperlipidemia.

7 Claims, No Drawings

BENZOXAZEPINE COMPOUNDS, THEIR PRODUCTION AND USE AS LIPID LOWERING AGENTS

This application is a 371 of PCT/JP96/02596, filed Sep. 12, 1996.

TECHNICAL FIELD

This invention relates to a benzoxazepine compound having an activity of lowering cholesterol-level and an activity of lowering triglyceride-level and useful for prophylaxis and therapy of hyperlipemia.

BACKGROUND ART

Abnormal increase of concentrations of lipids in plasma is called "hyperlipidemia" or "hyperlipemia". Serum lipids include cholesterol (cholesterol ester, free cholesterol), phospholipid (lecithin, sphingomyelin, etc.), triglyceride (neutral fat), free fatty acid and other sterols. Increase of cholesterol and triglyceride is especially taken up as a problem from the clinical viewpoint [cf. Common Disease Series No.19 Koshikessho (hyperlipemia) compiled by Haruo Nakamura, published by Nankodo].

Therefore, adequate control of lipid concentration in blood is remarkably important for the prophylaxis or therapy of various diseases related to arteriosclerosis typically exemplified by ischemic heart disease and cerebral infarction. And, hypertriglyceridemia is considered to accompany pancreatic disorders.

As pharmaceutical compositions for lowering cholesterol in blood, attention has been drawn to those for controlling the biosynthesis of cholesterol, besides those of inhibiting its absorption by binding bile acid including, among others, cholestyramine, colestipol (for example, U.S. Pat. No. 4,027,009), and those of suppressing the intestinal absorption of cholesterol by inhibiting acyl coenzyme A cholesterol acyl transferase (ACAT) including melinamide (French Patent No.1476569). As pharmaceutical preparations for controlling the biosynthesis of cholesterol, lovastatin (U.S. Pat. No. 4,231,938), simvastatin (U.S. Pat. No. 4,444,784), pravastatin (U.S. Pat. No. 4,346,227), etc., which are capable of inhibiting especially 3-hydroxy-3-methyl glutaryl coenzyme (HMG-CoA) reductase, are provided for medicinal use. However, when HMG-CoA reductase is inhibited, not only the biosynthesis of cholesterol but the biosynthesis of some other components such as ubiquinone, dolichol and heme A, which are necessary for the living body, is also inhibited, so that occurrences of undesirable side effects to be caused thereby are feared.

While, as agents of lowering triglyceride, fibrinoic acid type compounds, for example, clofibrate (UK Patent 860303) and fenofibrate (German Patent 2250327), are provided for medicines, they are prohibited to use together with statin type compounds for the fear of causing liver-toxicity.

Squalene synthetase is an enzyme taking part in the essential stage of the cholesterol biosynthetic pathway. This enzyme catalyzes the reductive dimerization of two molecules of farnesyl pyrophosphate to form squalene.

On the other hand, the compounds expected as inhibitors of cholesterol biosynthesis by inhibiting squalene synthetase are disclosed in Journal of Medicinal Chemistry, Vol.51, No.10, pp.1869–1871, 1988, JPA H1(1989)-213288, JPA H2(1990)-101088, JPA H2(1990)-235820, JPA H2(1990)-235821, JPA H3(1991)-20226, JPA H3(1991)-68591, JPA H3(1991)-148288, and U.S. Pat. Nos. 5,019,390, 5,135,935, WO9215579 and WO9309115.

Incidentally, hyperlipemia is also called "hyperlipoproteinemia" and is classified into the following six types (WHO classification) taking lipoproteins into consideration.

Type I: hyperchylomicronemia showing increase of chylomicrons,

Type IIa: hyperLDLemia (hypercholesterolemia) showing increase of low-density lipoprotein (LDL), Type IIb: composite hyperlipemia showing increase of LDL and very-low-density lipoprotein (VLDL), Type III: abnormal β lipoproteinemia showing the presence of β very-low-density lipoprotein (β VLDL), Type IV: endogenous hypertriglycerolemia, and Type V: mixed type hyperlipemia showing increase of VLDL and chylomicrons.

DISCLOSURE OF INVENTION

Through intensive investigations from the above viewpoints, the present inventors synthesized, for the first time, a 4,1-benzoxazepine compound with the characteristic feature having specific substituents at 1-, 3-, 5- and 7-positions, and found that this compound has unexpectedly excellent lipid-level lowering activity based on the specific chemical structure, thus accomplishing the present invention.

More specifically, the present invention relates to:

(1) a compound represented by the formula (I)

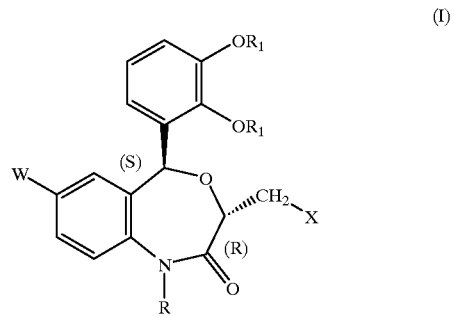

wherein R stands for a lower alkyl group optionally substituted by hydroxyl group which may be substituted, X stands for an optionally substituted carbamoyl group or an optionally substituted heterocyclic group having a deprotonatable hydrogen atom, $R_1$ stands for a lower alkyl group and W stands for a halogen atom, or a salt thereof, (2) the compound of (1) defined above, wherein R is $C_{1-6}$ alkyl which may have 1 to 3 substituents selected from the group consisting of hydroxyl, acetyloxy, propionyloxy, t-butoxycarbonyloxy, palmitoyloxy, dimethylaminoacetyloxy and 2-aminopropionyloxy, (3) the compound of (1) defined above, wherein R is $C_{3-6}$ branched alkyl which has 1 to 3 substituents selected from the group consisting of hydroxyl, acetyloxy, propionyloxy, t-butoxycarbonyloxy, palmitoyloxy, dimethylaminoacetyloxy and 2-aminopropionyloxy, (4) the compound of (1) defined above, wherein R is 2,2-dimethyl-3-hydroxypropyl, 3-hydroxy-2-hydroxymethyl-2-methylpropyl, 3-acetoxy-2,2-dimethylpropyl, 3-acetoxy-2-hydroxymethyl-2-methylpropyl or 3-acetoxy-2-acetoxymethyl-2-methylpropyl, (5) the compound of (1) defined above, wherein $R_1$ is methyl, (6) the compound of (1) defined above, wherein W is chlorine atom, (7) the compound of (1) defined above, wherein X is a carbamoyl group represented by the formula

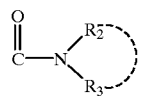

wherein $R_2$ and $R_3$ are independently
(i) hydrogen,
(ii) optionally substituted hydrocarbon group,
(iii) optionally substituted heterocyclic group, or
(iv) acyl group or $R_2$ and $R_3$ may form an optionally substituted 5 to 6 membered ring together with the adjacent nitrogen atom, said ring may contain 1 to 4 hetero atoms selected from nitrogen, oxygen and sulfur in addition to said nitrogen atom, (8) the compound of (7) defined above, wherein $R_2$ is hydrogen or $C_{1-7}$ alkyl, $R_3$ is 1) a hydrocarbon group selected from the group consisting of
   (a) $C_{1-7}$ alkyl,
   (b) $C_{3-7}$ cycloalkyl,
   (c) $C_{2-6}$ alkenyl,
   (d) $C_{6-10}$ aryl and
   (e) $C_{6-10}$ aryl-$C_{1-4}$ alkyl, wherein each of said groups (a), (b) and (c) may have 1 to 4 substituents selected from the group consisting of
   (i) carboxyl which may be esterified with $C_{1-6}$ alkyl or $C_{6-10}$ aryl-$C_{1-4}$ alkyl,
   (ii) phosphono group which may be mono- or di-substituted by $C_{1-6}$ alkyl or $C_{2-7}$ alkanoyloxy-$C_{1-6}$ alkyl,
   (iii) sulfo group,
   (iv) sulfonamido which may be substituted by $C_{1-6}$ alkyl or $C_{6-10}$ aryl-$C_{1-4}$ alkyl,
   (v) hydroxyl group which may be alkylated with $C_{1-3}$ alkyl,
   (vi) sulfhydryl group which may be alkylated with $C_{1-3}$ alkyl,
   (vii) carbamoyl,
   (viii) phenyl which may have 1 to 5 substituents selected from the group consisting of hydroxy, chlorine, fluorine, aminosulfonyl and amino which may be mono or di-substituted by $C_{1-3}$ alkyl,
   (ix) amino which may be mono- or di-substituted by $C_{1-3}$ alkyl,
   (x) cyclic amino group selected from the group consisting of piperidyl, pyrrolidinyl, morpholinyl, thiomorpholinyl, piperazinyl, 4-methylpiperazinyl, 4-benzylpiperazinyl, 4-phenylpiperazinyl, 1,2,3,4-tetrahydroisoquinolinyl and phthalimido, each of said group may be substituted by $C_{1-3}$ alkyl, benzyl or phenyl and
   (xi) 5- to 6-membered heterocyclic group selected from the group consisting of pyridinyl, imidazolyl, indolyl and tetrazolyl, and each of said group (d) and (e) may have 1 to 4 substituents selected from the group consisting of
   (i) carboxyl which may be esterified by $C_{1-4}$ alkyl,
   (ii) phosphono which may be mono- or di-substituted by $C_{1-6}$ alkyl or $C_{2-7}$ alkanoyloxy-$C_{1-6}$ alkyl,
   (iii) sulfo,
   (iv) $C_{1-4}$ alkylsulfonyl, $C_{6-10}$ arylsulfonyl or $C_{6-10}$ aryl-$C_{1-4}$ alkylsulfonyl,
   (v) sulfonamido which may be substituted by $C_{1-6}$ alkyl or $C_{6-10}$ aryl-$C_{1-4}$ alkyl,
   (vi) $C_{1-3}$ alkyl group which may be substituted by carboxyl group optionally esterified with $C_{1-4}$ alkyl, phosphono which may be mono- or di-substituted by $C_{1-6}$ alkyl, sulfo or sulfonamido which may be substituted by $C_{1-6}$ alkyl or $C_{6-10}$ aryl-$C_{1-4}$ alkyl and
   (vii) halogen, 2) a heterocyclic group selected from the group consisting of tetrazolyl, 4,5-dihydro-5-oxo-1,2,4-oxadiazolyl, 4,5-dihydro-5-thioxo-1,2,4-oxadiazolyl, 2,3-dihydro-3-oxo-1,2,4-oxadiazolyl, 2,3-dihydro-3-thioxo-1,2,4-oxadiazolyl, 3,5-dioxo-1,2,4-oxadiazolidinyl, 4,5-dihydro-5-oxo-isoxazolyl, 4,5-dihydro-5-thioxo-isoxazolyl, 2,3-dihydro-2-oxo-1,3,4-oxadiazolyl, 2,3-dihydro-3-oxo-1,2,4-triazolyl and 2,3-dihydro-3-thioxo-1,2,4-triazolyl or the salt thereof, 3) an acyl group selected from the group consisting of
   (i) $C_{2-7}$ alkanoyl which may be substituted by 1 to 2 halogen atoms,
   (ii) $C_{6-10}$ arylsulfonyl,
   (iii) $C_{1-4}$ alkylsulfonyl, and
   (iv) $C_{6-10}$ aryl-$C_{1-4}$ alkylsulfonyl, each of said group (ii), (iii) and (iv) may have 1 to 4 substituents selected from the group consisting of $C_{1-3}$ alkyl, $C_{1-3}$ alkoxy and halogen, or $R_2$ and $R_3$ together with adjacent nitrogen form a 5- or 6- membered cyclic amino selected from the group consisting of piperazinyl, piperidyl, pyrrolidinyl, 2-oxo-piperazinyl, 2,6-dioxopiperazinyl, morpholinyl and thiomorpholinyl, each of said group may have 1 to 4 substituents selected from the group consisting of
   (A) hydroxyl which may be substituted with $C_{1-3}$ alkyl or $C_{2-7}$ alkanoyl,
   (B) carboxyl which may be substituted with $C_{1-6}$ alkyl or $C_{6-10}$ aryl-$C_{1-4}$ alkyl,
   (C) phosphono which may be mono- or di-substituted by $C_{1-6}$ alkyl or $C_{2-7}$ alkanoyloxy-$C_{1-6}$ alkyl,
   (D) sulfo,
   (E) sulfonamide which may be substituted with $C_{1-6}$ alkyl or $C_{6-10}$ aryl-$C_{1-4}$ alkyl,
   (F) $C_{1-6}$ alkyl or $C_{2-5}$ alkenyl which may be substituted by
      (i) carboxyl group which may be esterified with $C_{1-6}$ alkyl or $C_{6-10}$ aryl-$C_{1-4}$ alkyl,
      (ii) phosphono group which may be mono- or di substituted by $C_{1-6}$ alkyl or $C_{2-7}$ alkanoyloxy-$C_{1-6}$ alkyl,
      (iii) sulfo group,
      (iv) sulfonamido which may be substituted by $C_{1-6}$ alkyl or $C_{6-10}$ aryl-$C_{1-4}$ alkyl,
      (v) hydroxyl group which may be alkylated with $C_{1-3}$ alkyl or $C_{2-7}$ alkanoyl,
      (vi) sulfhydryl group which may be alkylated with $C_{1-3}$ alkyl,
      (vii) carbamoyl,
      (viii) phenyl which may have 1 to 5 substituents selected from the group consisting of hydroxy, halogen, aminosulfonyl and amino which may be substituted with $C_{1-3}$ alkyl and (ix) amino which may be mono- or di-substituted by $C_{1-3}$ alkyl, or (x) tetrazolyl, (G) amino which may be mono- or di-substituted with $C_{1-3}$ alkyl, (H) cyclic amino group selected from the group consisting of piperidyl, pyrrolidinyl, morpholinyl, thiomorpholinyl, 4-methylpiperazinyl, 4-benzylpiperazinyl, and 4-phenylpiperazinyl, (I) cyano, (J) carbamoyl, (K) oxo, (L) heterocyclic group selected from tetrazolyl and 2,5-dihydro-5-oxo-1,2,4-oxadiazolyl, (M) carbamoyl substituted with $C_{1-4}$ alkylsulfonyl, $C_{6-10}$ arylsulfonyl or $C_{6-10}$ aryl-$C_{1-4}$ alkylsulfonyl, (N) sulfhydryl which may be alkylated with $C_{1-3}$ alkyl, (O) phenyl which may have 1 to 5 substituents selected from hydroxyl, halogen, aminosulfonyl and amino which may be substituted with $C_{1-3}$ alkyl, or the salt thereof, (9) the compound of (7) defined above, wherein $R_2$ and $R_3$ together with the adjacent nitrogen of the carbamoyl form a 5 to 6-membered ring selected from the group consisting of 1-piperazinyl, piperidyl, 1-pyrrolidinyl, 2-oxo-piperazinyl and 2,6-dioxo-piperazinyl, each of the said group may have 1 to 2 substituents of $C_{1-6}$ alkyl which may be substituted by (i) carboxyl which may be esterified with $C_{1-6}$ alkyl or $C_{6-10}$ aryl-$C_{1-4}$ alkyl, (ii) phosphono group which may be mono- or di-substituted by $C_{1-6}$ alkyl or $C_{2-7}$ alkanoyloxy-$C_{1-6}$ alkyl, (iii) sulfo group, (iv) sulfonamido which may be substituted by $C_{1-6}$ alkyl or $C_{6-10}$ aryl-$C_{1-4}$ alkyl, (v) hydroxyl group which may be alkylated by $C_{1-3}$ alkyl, (vi) sulfhydryl which may be alkylated by $C_{1-3}$ alkyl, (vii) carbamoyl, (viii) phenyl which may have 1 to 5 substituents selected from the group consisting of hydroxy, halogen, aminosulfonyl and amino which may be substituted with $C_{1-3}$ alkyl, (ix) amino which may be mono- or di-substituted by $C_{1-3}$ alkyl, or (x) tetrazolyl,

(10) the compound of (7) defined above, wherein $R_2$ is hydrogen or $C_{1-7}$ alkyl and $R_3$ is $C_{1-4}$ alkylsulfonyl,

(11) The compound of term (1) defined above, wherein the heterocyclic group represented by X is tetrazolyl, 4,5-dihydro-5-oxo-1,2,4-oxadiazolyl, 4,5-dihydro-5-thioxo-1,2,4-oxadiazolyl, 2,3-dihydro-3-oxo-1,2,4-oxadiazolyl, 2,3-dihydro-3-thioxo-1,2,4-oxadiazolyl, 3,5-dioxo-1,2,4-oxadiazolidinyl, 4,5-dihydro-5-oxo-isoxazolyl, 4,5-dihydro-5-thioxo-isoxazolyl, 2,3-dihydro-2-oxo-1,3,4-oxadiazolyl, 2,3-dihydro-3-oxo-1,2,4-triazolyl, or 2,3-dihydro-3-thioxo-1,2,4-triazolyl,

(12) the compound of (1) defined above, wherein $R_1$ is methyl, W is chlorine atom, R is $C_{3-6}$ branched alkyl which has 1 to 3 substituents selected from the group consisting of hydroxyl, acetyloxy, propionyloxy, t-butoxycarbonyloxy, palmitoyloxy, dimethylaminoacetyloxy and 2-aminopropionyloxy, and X is the carbamoyl group represented by a formula

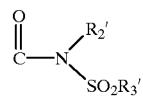

wherein $R_2'$ is hydrogen or $C_{1-7}$ alkyl and $R_3'$ is $C_{1-4}$ alkyl,

(13) the compound of (1) defined above, wherein $R_1$ is methyl, W is chlorine atom, R is $C_{3-6}$ branched alkyl which has 1 to 3 substituents selected from the group consisting of hydroxyl, acetyloxy, propionyloxy, t-butoxycarbonyloxy, palmitoyloxy, dimethylaminoacetyloxy and 2-aminopropionyloxy, and X is the carbamoyl group represented by a formula

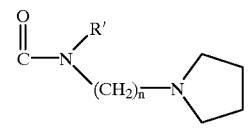

wherein R' is hydrogen or $C_{1-7}$ alkyl and n is an integer from 1 to 5,

(14) the compound of (1) defined above, wherein $R_1$ is methyl, W is chlorine atom, R is $C_{3-6}$ branched alkyl which has 1 to 3 substituents selected from the group consisting of hydroxyl, acetyloxy, propionyloxy, t-butoxycarbonyloxy, palmitoyloxy, dimethylaminoacetyloxy and 2-aminopropionyloxy, and X is a carbamoyl group represented by the formula

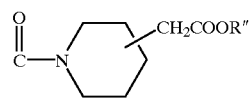

wherein R" is hydrogen or $C_{1-4}$ alkyl,

(15) the compound of (1) defined above, wherein $R_1$ is methyl, W is chlorine atom, R is $C_{3-6}$ branched alkyl which has 1 to 3 substituents selected from the group consisting of hydroxyl, acetyloxy, propionyloxy, t-butoxycarbonyloxy, palmitoyloxy, dimethylaminoacetyloxy and 2-aminopropionyloxy, and X is tetrazolyl,

(16) the compound of (1) defined above, which is (3R,5S)-N-methanesulfonyl-7-chloro-5-(2,3-dimethoxyphenyl)-1-(3-hydroxy-2,2-dimethylpropyl)-2-oxo-1,2,3,5-tetrahydro-4,1-benzoxazepine-3-acetamide, (3R,5S)-N-methanesulfonyl-7-chloro-5-(2,3-dimethoxyphenyl)-1-(3-hydroxy-2-hydroxymethyl-2-methylpropyl)-2-oxo-1,2,3,5-tetrahydro-4,1-benzoxazepine-3-acetamide, (3R,5S)-7-chloro-5-(2,3-dimethoxyphenyl)-1-(3-hydroxy-2-hydroxymethyl-2-methylpropyl)-2-oxo-N-[2-(pyrrolidin-1-yl)ethyl]-1,2,3,5-tetrahydro-4,1-benzoxazepine-3-acetamide, (3R,5S)-7-chloro-5-(2,3-dimethoxyphenyl)-1-(3-hydroxy-2,2-dimethylpropyl)-2-oxo-N-[2-(pyrrolidin-1-yl)ethyl]-1,2,3,5-tetrahydro-4,1-benzazepine-3-acetamide, or a salt thereof,

(17) the compound of (1) defined above, which is (3R,5S)-N-methanesulfonyl-1-(3-acetoxy-2,2-dimethylpropyl)-7-chloro-5-(2,3-dimethoxyphenyl)-2-oxo-1,2,3,5-tetrahydro-4,1-benzoxazepine-3-acetamide, (3R,5S)-N-methanesulfonyl-1-(3-acetoxy-2-acetoxymethyl-2-methylpropyl)-7-chloro-5-(2,3-dimethoxyphenyl)-2-oxo-1,2,3,5-tetrahydro-4,1-benzoxazepine-3-acetamide, N-[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepine-3-acetyl]piperidine-4-acetic acid, N-[(3R,5S)-1-(3-acetoxy-2-acetoxymethyl-2-methylpropyl)-7-chloro-5-(2,3-dimethoxyphenyl)-2-oxo-1,2,3,5-tetrahydro-4,1-benzoxazepine-3-acetyl] piperidine-4-acetic acid, N-[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepine-3-acetyl]piperidine-4-acetic acid ethyl ester, N-[(3R,5S)-1-(3-acetoxy-2-acetoxymethyl-2-methylpropyl)-7-chloro-5-(2,3-dimethoxyphenyl)-2-oxo-1,2,3,5-tetrahydro-4,1-benzoxazepine-3-acetyl] piperidine-4-acetic acid ethyl ester or a salt thereof,

(18) the compound of (1) defined above, which is (3R,5S)-7-chloro-5-(2,3-dimethoxyphenyl)-1-(3-hydroxy-2,2-dimethylpropyl)-1,2,3,5-tetrahydro-3-[1H(or3H)-tetrazol-5-yl]methyl-4,1-benzoxazepine-2-one, (3R,5S)-7-chloro-5-(2,3-dimethoxyphenyl)-1-(3-hydroxy-2-hydroxymethyl-2-methylpropyl)-1,2,3,5-tetrahydro-3-[1H(or3H)-tetrazol-5-yl]methyl-4,1-benzoxazepine-2-one, (3R,5S)-1-(3-acetoxy-2,2-dimethylpropyl)-7-chloro-5-(2,3-dimethoxyphenyl)-1,2,3,5-tetrahydro-3-[1H(or3H)-tetrazol-5-yl]methyl-4,1-benzoxazepine-2-one, (3R,5S)-1-(3-acetoxy-2-acetoxymethyl-2-methylpropyl)-7-chloro-5-(2,3-dimethoxyphenyl)-1,2,3,5-tetrahydro-3-[1H(or3H)-tetrazol-5-yl]methyl-4,1-benzoxazepine-2-one or a salt thereof,

(19) the compound of (1) defined above, which is (3R,5S)-7-Chloro-5-(2,3-dimethoxyphenyl)-1-neopentyl-2-oxo-N-[2-(pyrrolidin-1-yl)ethyl]-1,2,3,5-tetrahydro-4,1-benzoxazepine-3-acetamide or the salt thereof,

(20) the compound of (1) defined above, wherein

R is a lower alkyl group which may be substituted with one or two hydroxyl groups, X is carbamoyl group, which may have substituent(s) on the nitrogen atom of the carbamoyl group, said substituent being (1) hydrocarbon selected from the group consisting of (a) $C_{1-7}$ alkyl, (b) $C_{3-7}$ cycloalkyl, (c) $C_{2-6}$ alkenyl, (d) $C_{6-10}$ aryl and (e) $C_{7-14}$ arylalkyl ($C_{6-10}$ aryl-$C_{1-4}$ alkyl), wherein each of said groups (a), (b) and (c) may have 1 to 4 substituents selected from the group consisting of (i) carboxyl which may be esterified with $C_{1-6}$ alkyl or $C_{7-10}$ arylalkyl (phenyl-$C_{1-4}$ alkyl), (ii) phosphono group, (iii) sulfo group, (iv) sulfonamido which may be substituted by $C_{1-6}$ alkyl or $C_{7-10}$ arylalkyl (phenyl-$C_{1-4}$ alkyl), (v) hydroxyl group which may be alkylated with $C_{1-3}$ alkyl, (vi) sulfhydryl group which may be alkylated with $C_{1-3}$ alkyl, (vii) carbamoyl, (viii) phenyl which may have substituent(s) selected from the group consisting of hydroxyl, chlorine, fluorine, aminosulfonyl and amino which may be mono or di-substituted by $C_{1-3}$ alkyl, (ix) amino which may be mono- or di-substituted by $C_{1-3}$ alkyl, (x) cyclic amino group selected from the group consisting of piperidyl, pyrrolidinyl, morpholinyl, thiomorpholinyl, piperazinyl, 4-methylpiperazinyl, 4-benzylpiperazinyl and 4-phenylpiperazinyl, each of said group may be substituted by $C_{1-3}$ alkyl, benzyl or phenyl and (xi) 5- to 6-membered heterocyclic group selected from the group consisting of pyridinyl, imidazolyl, indolyl and tetrazolyl, and each of said group (d) and (e) may have 1 to 4 substituents selected from the group consisting of (i) carboxyl which may be esterified by $C_{1-4}$ alkyl, (ii) phosphono, (iii) sulfo, (iv) sulfonamido which may be substituted by $C_{1-6}$ alkyl or $C_{7-10}$ arylalkyl (phenyl-$C_{1-4}$ alkyl), (v) $C_{1-3}$ alkyl group which may be substituted by carboxyl group optionally esterified with $C_{1-4}$ alkyl, phosphono, sulfo, or sulfonamido optionally substituted with $C_{1-6}$ alkyl or $C_{7-10}$ arylalkyl (phenyl-$C_{1-4}$ alkyl), and (vi) halogen, (2) a heterocyclic group selected from the group consisting of tetrazolyl, 4,5-dihydro-5-oxo-1,2,4-oxadiazolyl, 4,5-dihydro-5-thioxo-1,2,4-oxadiazolyl, 2,3-dihydro-3-oxo-1,2,4-oxadiazolyl, 2,3-dihydro-3-thioxo-1,2,4-oxadiazolyl, 3,5-dioxo-1,2,4-oxadiazolidinyl, 4,5-dihydro-5-oxo-isoxazolyl, 4,5-dihydro-5-thioxo-isoxazolyl, 2,3-dihydro-2-oxo-1,3,4-oxadiazolyl, 2,3-dihydro-3-oxo-1,2,4-triazolyl and 2,3-dihydro-3-thioxo-1,2,4-triazolyl, (3) an acyl group selected from the group consisting of (i) $C_{2-7}$ alkanoyl which may be substituted by 1 to 2 halogen atoms, (ii) $C_{6-10}$ arylsulfonyl, (iii) $C_{1-4}$ alkylsulfonyl, and (iv) $C_{7-14}$ arylalkylsulfonyl ($C_{6-10}$ aryl-$C_{1-4}$ alkylsulfonyl), each of said group (ii), (iii) and (iv) may have 1 to 4 substituents selected from the group consisting of $C_{1-3}$ alkyl, $C_{1-3}$ alkoxy and halogen or (4) cyclic amino carbonyl group, the cyclic amino group being selected from the group consisting of piperazinyl, piperidyl, pyrrolidinyl, 2-oxo-piperazinyl, 2,6-dioxopiperazinyl, morpholinyl and thiomorpholinyl, each of said group may have 1 to 4 substituents selected from the group consisting of (i) hydroxyl, (ii) carboxyl optionally esterified with $C_{1-4}$ alkyl, (iii) phosphono, (iv) sulfo, (v) sulfonamido optionally substituted with $C_{1-6}$ alkyl or $C_{7-10}$ arylalkyl (phenyl-$C_{1-4}$ alkyl), (vi) $C_{1-3}$ alkyl or $C_{2-5}$ alkenyl optionally substituted with (i), (ii), (iii), (iv) or (v) defined above, (vii) amino optionally mono- or di-substituted with $C_{1-3}$ alkyl, (viii) cyclic amino group selected from piperidyl, pyrrolidinyl, morpholinyl, thiomorpholinyl, 4-methylpiperazinyl, 4-benzylpiperazinyl and 4-phenylpiperazinyl, (ix) cyano, (x) carbamoyl, (xi) oxo, (xii) $C_{1-3}$ alkoxy, (xiii) heterocyclic group selected from tetrazolyl and 2,5-dihydro-5-oxo-1,2,4-oxadiazolyl, and (xiv) carbamoyl substituted with $C_{6-10}$ arylsulfonyl, $C_{1-4}$ alkylsulfonyl or $C_{7-10}$ arylalkylsulfonyl (phenyl-$C_{1-4}$ alkylsulfonyl),

(21) a composition which comprises the compound of (1) defined above and a pharmaceutically acceptable carrier,

(22) a pharmaceutical composition for inhibiting squalene synthetase, which comprises the compound of (1) defined above and a pharmaceutically acceptable carrier,

(23) a pharmaceutical composition for lowering the level of triglyceride, which comprises the compound of (1) defined above and a pharmaceutically acceptable carrier,

(24) a pharmaceutical composition for lowering the lipid-level, which comprises the compound of (1) defined above and a pharmaceutically acceptable carrier,

(25) a pharmaceutical composition for prophylaxis or therapy of hyperlipidaemia, which comprises the compound of (1) defined above and a pharmaceutically acceptable carrier,

(26) use of the compound of (1) defined above for manufacturing a pharmaceutical composition,

(27) use of the compound of (1) defined above for manufacturing a squalene synthetase inhibitor,

(28) use of the compound of (1) defined above for manufacturing a pharmaceutical composition for lowering the level of triglyceride,

(29) use of the compound of (1) defined above for manufacturing a pharmaceutical composition for lowering the lipid-level,

(30) use of the compound of (1) defined above for manufacturing a pharmaceutical composition for prophylaxis or therapy of hyperlipidaemia or coronary sclerosis,

(31) a method for inhibiting squalene synthetase in a mammal comprising administering an effective amount of the compound of (1) defined above to said mammal,

(32) a method for lowering the level of triglyceride in a mammal comprising administering an effective amount of the compound of (1) defined above to said mammal,

(33) a method for lowering the lipid-level in a mammal comprising administering an effective amount of the compound of (1) defined above to said mammal,

(34) a method for prophylaxis or therapy of hyperlipidaemia or coronary sclerosis in a mammal comprising administering an effective amount of the compound of (1) defined above to said mammal,

(35) a process for producing the compound or the salt thereof of (1) defined above, wherein X is an optionally substituted carbamoyl group, which comprises reacting a compound of the formula:

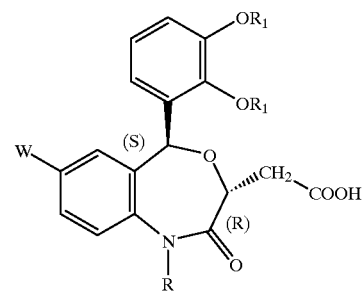

wherein the symbols are the same as defined in term (1), or a salt thereof with a compound of the formula:

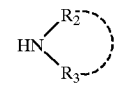

wherein the symbols are the same as defined in (7), or a salt thereof,

(36) the compound of (1) defined above, wherein R is 2,2-dimethyl-3-hydroxypropyl.

As the lower alkyl group shown by R, mention is made of $C_{1-6}$ alkyl such as methyl, ethyl, n-propyl, isopropyl, n-butyl, isobutyl, n-pentyl, isopentyl, neopentyl and hexyl. Above all, $C_{3-6}$ alkyl groups are preferable and $C_{4-5}$ alkyl groups are more preferable. Especially, branched $C_{4-5}$ alkyl groups such as isobutyl and neopentyl are most preferable. The substituent of lower alkyl group shown by R includes hydroxyl group which may be substituted with for example $C_{2-20}$ alkanoyl, $C_{1-7}$ alkyl and so on. Specifically, the substituent of lower alkyl group shown by R includes hydroxyl, acetyloxy, propionyloxy, t-butoxycarbonyloxy, palmitoyloxy, dimethylaminoacetyloxy and 2-aminopropionyloxy. The number of the above substituents ranges from 1 to 3.

Examples of R include 2,2-dimethyl-3-hydroxypropyl, 3-hydroxy-2-hydroxymethyl-2-methylpropyl, 3-acetoxy-2,2-dimethylpropyl, 3-acetoxy-2-hydroxymethyl-2-methylpropyl and 3-acetoxy-2-acetoxymethyl-2-methylpropyl.

The "optionally substituted carbamoyl group" is represented by the formula

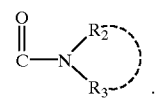

The term "hydrocarbon group" described in the specification includes optionally substituted $C_{1-7}$ straight-chain or branched alkyl groups (e.g. methyl, ethyl, n-propyl, isopropyl, n-butyl, isobutyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 2-ethylbutyl, 1-ethylbutyl, neopentyl, hexyl and heptyl), optionally substituted $C_{3-7}$ cycloalkyl groups (e.g. cyclopropyl, cyclobutyl, cyclopentyl, cyclohexyl and cyclohexylmethyl), optionally substituted $C_{2-6}$ straight-chain or branched alkenyl groups (e.g. vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl), optionally substituted $C_{6-10}$ aryl groups (e.g. phenyl and naphthyl groups) and optionally substituted $C_{6-10}$ aryl-$C_{1-4}$ alkyl groups (e.g. benzyl, phenethyl and naphthylmethyl).

Substituents of "optionally substituted $C_{1-7}$ straight-chain or branched alkyl groups, optionally substituted $C_{3-7}$ cycloalkyl groups and $C_{2-6}$ straight-chain or branched alkenyl groups" are exemplified by carboxyl groups optionally esterified with $C_{1-6}$ alkyl groups or $C_{6-10}$ aryl-$C_{1-4}$ alkyl groups (e.g. methyl, ethyl, propyl, isopropyl, butyl, t-butyl, phenyl and benzyl), phosphono group which may be mono- or di-substituted by $C_{1-6}$ alkyl such as methyl, ethyl, n-propyl, isopropyl, n-butyl, isobutyl, n-pentyl, isopentyl, neopentyl and hexyl, or $C_{2-7}$ alkanoyloxy-$C_{1-6}$ alkyl such as acetyloxy methyl and pivaloyloxymethyl, sulfo group, sulfonamido group optionally substituted with $C_{1-6}$ alkyl groups or $C_{6-10}$ aryl-$C_{1-4}$ alkyl groups (e.g. methyl, ethyl, propyl, isopropyl, butyl, t-butyl and benzyl), hydroxyl group and sulfhydryl group optionally alkylated with $C_{1-3}$ alkyl groups (e.g. methyl, ethyl and propyl), carbamoyl group, phenyl group optionally substituted with 1 to 5 substituents [e.g. hydroxyl group, chlorine, fluorine, aminosulfonyl group, and amino group optionally substituted with $C_{1-3}$ alkyl group (e.g. methyl, ethyl and propyl)], amino group optionally mono- or di-substituted with $C_{1-3}$ alkyl groups (e.g. methyl, ethyl and propyl), cyclic amino groups which may further have a hetero atom selected from oxygen and sulfur as the ring-forming atoms, and which may be substituted by $C_{1-3}$ alkyl, benzyl or phenyl, such as (piperidyl, pyrrolidinyl, morpholinyl, thiomorpholinyl, piperazinyl, 4-methylpiperazinyl, 4-benzylpiperazinyl, 4-phenylpiperazinyl, 1,2,3,4-tetrahydroisoquinolinyl, and phthalimido) and aromatic 5- to 6-membered heterocyclic groups containing 1 to 4 hetero-atoms selected from N, O and S (e.g. pyridinyl, imidazolyl, indolyl and tetrazolyl).

Further, examples of the substituents of $C_{6-10}$ aryl groups and $C_{6-10}$ aryl-$C_{1-4}$ alkyl groups as the substituents of the optionally substituted amino groups forming the carbamoyl group of "optionally substituted carbamoyl groups" shown by X include carboxyl groups optionally esterified with $C_{1-4}$ alkyl groups (e.g. methyl, ethyl, propyl and t-butyl groups), phosphono group which may be mono- or di-substituted by $C_{1-6}$ alkyl such as methyl, ethyl, n-propyl, isopropyl, n-butyl, isobutyl, n-pentyl, isopentyl, neopentyl and hexyl, or or $C_{2-7}$ alkanoyloxy-$C_{1-6}$ alkyl such as acetyloxy methyl and pivaloyloxymethyl, sulfo group, $C_{1-4}$ alkylsulfonyl (e.g. methylsulfonyl, ethylsulfonyl, n-propylsulfonyl, isopropylsulfonyl and n-butylsulfonyl), $C_{6-10}$ arylsulfonyl (e.g. phenylsulfonyl and naphthylsulfonyl) or $C_{6-10}$ aryl-$C_{1-4}$ alkylsulfonyl (e.g. benzylsulfonyl, phenethylsulfonyl and naphthylmethylsulfonyl), sulfonamido groups optionally substituted with $C_{1-6}$ alkyl groups or $C_{6-10}$ aryl-$C_{1-4}$ alkyl groups (e.g. methyl, ethyl, propyl, isopropyl, butyl, t-butyl and benzyl), and $C_{1-3}$ alkyl groups (e.g. methyl, ethyl, propyl and isopropyl) optionally substituted with (i) carboxyl groups optionally esterified with $C_{1-4}$ alkyl group (e.g. methyl, ethyl, propyl and butyl), (ii) phosphono group which may be mono- or di-substituted by $C_{1-6}$ alkyl such as methyl, ethyl, n-propyl, isopropyl, n-butyl, isobutyl, n-pentyl, isopentyl, neopentyl and hexyl, or $C_{2-7}$ alkanoyloxy-$C_{1-6}$ alkyl such as acetyloxymethyl and pivaloyloxymethyl, (iii) sulfo group and (iv) sulfonamido group optionally substituted with $C_{1-6}$ alkyl (e.g. methyl, ethyl, propyl, butyl, pentyl and hexyl) or $C_{6-10}$ aryl-$C_{1-4}$ alkyl (benzyl and phenethyl), and halogen (fluorine and chlorine).

The number of the substituents of "optionally substituted hydrocarbon group" is 1 to 4, preferably 1 to 2.

Preferable examples of "optionally substituted heterocyclic groups" described in the specification include heterocyclic groups having deprotonizable hydrogen atom optionally having one or two, preferably one, substituents of substituents such as oxo group and thioxo groups. As such heterocyclic groups, 5- to 6-membered heterocyclic groups consisting of 1 to 4, preferably 2 to 3, hetero-atoms selected from S, O and N are preferable. Specifically, tetrazolyl, 4,5-dihydro-5-oxo-1,2,4-oxadiazolyl, 4,5-dihydro-5-thioxo-1,2,4-oxadiazolyl, 2,3-dihydro-3-oxo-1,2,4-oxadiazolyl, 2,3-dihydro-3-thioxo-1,2,4-oxadiazolyl, 3,5-dioxo-1,2,4-oxadiazolidinyl, 4,5-dihydro-5-oxo-isoxazolyl, 4,5-dihydro-5-thioxo-isoxazolyl, 2,3-dihydro-2-oxo-1,3,4-oxadiazolyl, 2,3-dihydro-3-oxo-1,2,4-triazolyl and 2,3-dihydro-3-thioxo-1,2,4-triazolyl are exemplified. Especially tetrazolyl is preferable.

The term "acyl group" described in the specification refers to carboxylic acid acyl groups derived from carboxylic acid ($C_{2-7}$ carboxylic acid acyl group e.g. acetyl, propionyl, butyryl and benzoyl) and optionally substituted $C_{6-10}$ arylsulfonyl groups, $C_{1-4}$ alkylsulfonyl groups and $C_{6-10}$ aryl-$C_{1-4}$ alkylsulfonyl groups (e.g. methylsulfonyl, ethylsulfonyl, phenylsulfonyl, naphthylsulfonyl, phenylmethylsulfonyl, phenylethylsulfonyl, naphthylmethylsulfonyl and naphthylethylsulfonyl). As the substituents of aryl-, alkyl- and arylalkylsulfonyl groups, mention is made of, for example, $C_{1-3}$ alkyl (e.g. methyl, ethyl and propyl), $C_{1-3}$ alkoxy (e.g. methoxy, ethoxy and propoxy), halogen (chlorine, fluorine and bromine), and 1 to 4, preferably 1 to 2, of them may optionally be substituted at any substitutable position.

The above-mentioned carboxylic acid acyl groups may optionally have 1 to 2 halogen atoms (chlorine, fluorine and bromine) as substituents.

The ring formed by $R_2$ and $R_3$ together with the adjacent nitrogen of the carbamoyl refers to optionally substituted 5- or 6-membered cyclic amino which may further have 1 to 3 hetero atoms selected from nitrogen, sulfur and oxygen as ring constituting atoms such as piperazinyl, piperidino, 1-pyrrolidinyl, 2-oxo-1-piperazinyl, 2,6-dioxo-1-piperazinyl, morpholinyl and thiomorpholinyl. These cyclic amino groups may optionally have 1 to 4, preferably 1 to 2, substituents. Examples of those substituents include hydroxyl group which may be substituted with $C_{1-3}$ alkyl or $C_{2-7}$ alkanoyl, carboxyl groups optionally esterified with a $C_{1-4}$ alkyl group (e.g. methyl, ethyl, propyl or t-butyl group) or $C_{6-10}$ aryl-$C_{1-4}$ alkyl, phosphono group which may be mono- or di-substituted by $C_{1-6}$ alkyl such as methyl, ethyl, n-propyl, isopropyl, n-butyl, isobutyl, n-pentyl, isopentyl, neopentyl and hexyl or $C_{2-7}$ alkanoyloxy-$C_{1-6}$ alkyl such as acetyloxymethyl and pivaloyloxymethyl, sulfo group and sulfonamido group optionally substituted with a $C_{1-6}$ alkyl group or a $C_{6-10}$ aryl-$C_{1-4}$ alkyl group (e.g. methyl, ethyl, propyl, isopropyl, butyl, t-butyl or benzyl), $C_{1-6}$ alkyl which may be substituted by (i) carboxyl group which may be esterified with $C_{1-6}$ alkyl, or $C_{6-10}$ aryl-$C_{1-4}$ alkyl,
(ii) phosphono group which may be mono- or di substituted by $C_{1-6}$ alkyl or $C_{2-7}$ alkanoyloxy-$C_{1-6}$ alkyl,
(iii) sulfo group,
(iv) sulfonamido which may be substituted by $C_{1-6}$ alkyl or $C_{6-10}$ aryl-$C_{1-4}$ alkyl,
(v) hydroxyl group which may be alkylated with $C_{1-3}$ alkyl or $C_{2-7}$ alkanoyl,
(vi) sulfhydryl group which may be alkylated with $C_{1-3}$ alkyl,
(vii) carbamoyl,
(viii) phenyl which may have 1 to 5 substituents selected from the group consisting of hydroxy, halogen, aminosulfonyl, amino which may be substituted with $C_{1-3}$ alkyl and
(ix) amino which may be mono- or di-substituted by $C_{1-3}$ alkyl, or
(x) tetrazolyl, and $C_{2-5}$ alkenyl group (e.g. vinyl and allyl) which may be substituted by the same group selected among (i) to (x) as described above for substituents of $C_{1-6}$ alkyl, amino groups optionally mono- or di-substituted with $C_{1-3}$ alkyl groups, cyclic amino groups derived from 5- or 6-membered cyclic amine which may further have a hetero atom selected from nitrogen, sulfur and oxygen, and which may be substituted by $C_{1-3}$ alkyl, benzyl or phenyl, such as piperidyl, pyrrolidinyl, morpholinyl, thiomorpholinyl, 4-methylpiperazinyl, 4-benzylpiperazinyl and 4-phenylpiperazinyl, cyano group, carbamoyl group, oxo group, hetereocyclic groups optionally substituted with an oxo group or thioxo group having such a deprotonizable hydrogen atom as mentioned above (e.g. tetrazolyl and 2,5-dihydro-5-oxo-1,2,4-oxazolyl), carbamoyl groups substituted with $C_{1-4}$ alkylsulfonyl, $C_{6-10}$ arylsulfonyl and $C_{6-10}$ aryl-$C_{1-4}$ alkyl arylsulfonyl (methylsulfonyl, ethylsulfonyl, propylsulfonyl, butylsulfonyl, isopropylsulfonyl, t-butylsulfonyl, phenylsulfonyl and benzylsulfonyl), sulfhydryl which may be alkylated with $C_{1-3}$ alkyl and phenyl which may have 1 to 5 substituents such as hydroxyl, halogen, aminosulfonyl and amino which may be substituted with $C_{1-3}$ alkyl.

Examples of "optionally substituted carbamoyl group" shown by X include

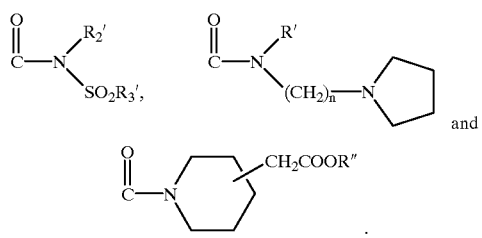

and

Examples of $R_2'$ and R' include hydrogen and $C_{1-7}$ alkyl. Among them, hydrogen is preferable.

Examples of $R_3'$ include $C_{1-4}$ alkyl such as methyl, ethyl, propyl and butyl.

Examples of $C_{1-7}$ alkyl shown by $R_2$, $R_2'$, R' are the same as those described in "hydrocarbon group".

Examples of R" include hydrogen and $C_{1-4}$ alkyl. Among them, hydrogen is preferable.

Examples of $C_{1-4}$ alkyl shown by $R_3'$ and R" include methyl, ethyl, propyl, isopropyl, n-butyl and t-butyl.

Examples of n include 1, 2, 3, 4 and 5.

Preferable examples of optionally substituted heterocyclic groups having deprotonizable hydrogen atom, shown by X, include N-containing (preferably 1 to 4 nitrogen atoms) 5- to 6-membered heterocyclic groups having Brønsted acid-like active proton, and those comprising 1 to 4, preferable 2 or 3, nitrogen atom, sulfur atom and oxygen atom, are preferable. As these substituents, mention is made of, for example, oxo group and thioxo group, and one or two, preferably one substituents may be present. As "optionally substituted heterocyclic groups having deprotonizable hydrogen atom" shown by X, mention is made of, for example, those exemplified as "optionally substituted heterocyclic groups" as the substituents of the "optionally substituted carbamoyl groups" shown by X, such as tetrazolyl, 2,5-dihydro-5-oxo-1,2,4-oxadiazolyl.

As "lower alkyl groups" shown by $R_1$, mention is made of $C_{1-6}$ alkyl groups such as methyl, ethyl, n-propyl, isopropyl, n-butyl, t-butyl, pentyl and hexyl. Among them, $C_{1-3}$ alkyl groups are especially preferable. As $R_1$, methyl group is especially preferable from the viewpoint of pharmacological activity.

As "halogen atoms" shown by W, mention is made of chlorine, fluorine, bromine and iodine atom. Among them, chlorine atom is especially preferable.

Specifically the following compounds are preferable:

(3R,5S)-N-methanesulfonyl-7-chloro-5-(2,3-dimethoxyphenyl)-1-(3-hydroxy-2,2-dimethylpropyl)-2-oxo-1,2,3,5-tetrahydro-4,1-benzoxazepine-3-acetamide, (3R,5S)-N-methanesulfonyl-7-chloro-5-(2,3-dimethoxyphenyl)-1-(3-hydroxy-2-hydroxymethyl-2-methylpropyl)-2-oxo-1,2,3,5-tetrahydro-4,1-benzoxazepine-3-acetamide, (3R,5S)-7-chloro-5-(2,3-dimethoxyphenyl)-1-(3-hydroxy-2-hydroxymethyl-2-methylpropyl)-2-oxo-N-[2-(pyrrolidin-1-yl)ethyl]-1,2,3,5-tetrahydro-4,1-benzoxazepine-3-acetamide, (3R,5S)-7-chloro-5-(2,3-dimethoxyphenyl)-1-(3-hydroxy-2,2-dimethylpropyl)-2-oxo-N-[2-(pyrrolidin-1-yl)ethyl]-1,2,3,5-tetrahydro-4,1-benzazepine-3-acetamide, (3R,5S)-N-methanesulfonyl-1-(3-acetoxy-2,2-dimethylpropyl)-7-chloro-5-(2,3-dimethoxyphenyl)-2-oxo-1,2,3,5-tetrahydro-4,1-benzoxazepine-3-acetamide, (3R,5S)-N-methanesulfonyl-1-(3-acetoxy-2-acetoxymethyl-2-methylpropyl)-7-chloro-5-(2,3-dimethoxyphenyl)-2-oxo-1,2,3,5-tetrahydro-4,1-benzoxazepine-3-acetamide, N-[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepine-3-acetyl]piperidine-4-acetic acid, N-[(3R,5S)-1-(3-acetoxy-2-acetoxymethyl-2-methylpropyl)-7-chloro-5-(2,3-dimethoxyphenyl)-2-oxo-1,2,3,5-tetrahydro-4,1-benzoxazepine-3-acetyl]piperidine-4-acetic acid, N-[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepine-3-acetyl]piperidine-4-acetic acid ethyl ester, N-[(3R,5S)-1-(3-acetoxy-2-acetoxymethyl-2-methylpropyl)-7-chloro-5-(2,3-dimethoxyphenyl)-2-oxo-1,2,3,5-tetrahydro-4,1-benzoxazepine-3-acetyl]piperidine-4-acetic acid ethyl ester, (3R,5S)-7-chloro-5-(2,3-dimethoxyphenyl)-1-(3-hydroxy-2,2-dimethylpropyl)-1,2,3,5-tetrahydro-3-[1H(or 3H)tetrazol-5-yl]methyl-4,1-benzoxazepine-2-one, (3R,5S)-7-chloro-5-(2,3-dimethoxyphenyl)-1-(3-hydroxy-2-hydroxymethyl-2-methylpropyl)-1,2,3,5-tetrahydro-3-[1H(or3H)-tetrazol-5-yl]methyl-4,1-benzoxazepine-2-one, (3R,5S)-1-(3-acetoxy-2,2-dimethylpropyl-7-chloro-5-(2,3-dimethoxyphenyl)-1,2,3,5-tetrahydro-3-[1H(or 3H)-tetrazol-5-yl]methyl-4,1-benzoxazepine-2-one, (3R,5S)-1-(3-acetoxy-2-acetoxymethyl-2-methylpropyl)-7-chloro-5-(2,3-dimethoxyphenyl)-1,2,3,5-tetrahydro-3-[1H(or 3H)-tetrazol-5-yl]methyl-4,1-benzoxazepine-2-one, (3R,5S)-7-chloro-5-(2,3-dimethoxyphenyl)-1-neopentyl-2-oxo-N-[2-(pyrrolidin-1-yl)ethyl]-1,2,3,5-tetrahydro-4,1-benzoxazepine-3-acetamide, etc.

As salts of the compound (I), mention is made of pharmaceutically acceptable salts including inorganic salts such as hydrochloride, hydrobromide, sulfate, nitrate and phosphate, organic acid salts such as acetate, tartrate, citrate, fumarate, maleate, toluenesulfonate and methanesulfonate, metal salts such as sodium salt, potassium salt, calcium salt and aluminum salt, and basic salts such as triethylamine salt, guanidine salt, ammonium salt, hydrazine salt, quinine salt and cinchonine salt.

Hydrate and non-hydrate of compound (I) are also concluded in the scope of this invention.

In the compound represented by the formula (I) or salts thereof, asymmetric carbons exist at 3- and 5-positions, and trans-compounds, in which the substituent at 3-position and substituent at 5-position are faced to the reverse direction relative to the face of the 7-membered ring, is preferable. Especially, those in which the absolute configuration at 3-position is R-configuration and the absolute configuration at 5-position is S-configuration, are preferable.

While the compound represented by the above-mentioned formula (I) or salts thereof can be produced in accordance with, for example, methods disclosed in EPA567026, WO95/21834 [PCT application based on Japanese Patent Application H6(1994)-15531)], EPA645377 [application based on Japanese Patent Application H6(1994)-229159] and EPA645378[application based on Japanese Patent Application H6(1994)-229160], or methods analogous to them, they can be produced also by, for example, the following methods.

More specifically, the compound of the formula (I) or a salt thereof can be produced, as shown by, for example, the following formula, by subjecting a corresponding 3-carboxymethyl compound (I') to condensation with a compound represented by the formula

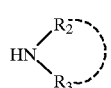

($R_2$ and $R_3$ are defined above)

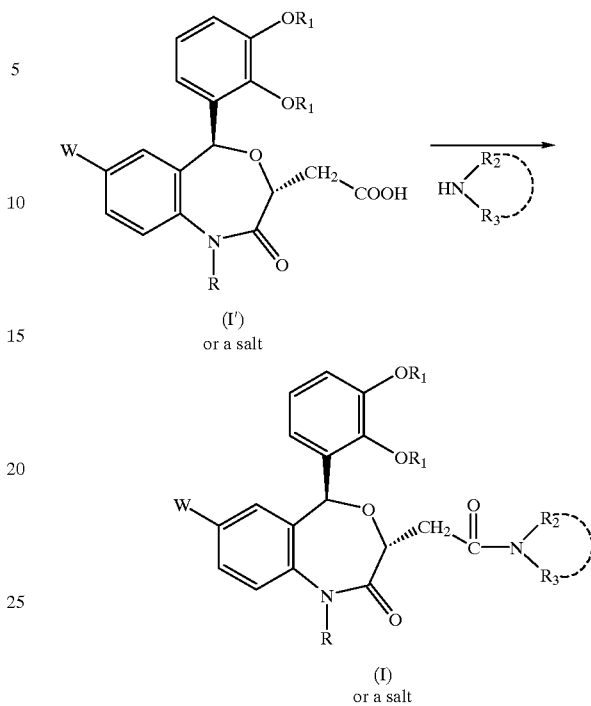

[wherein each symbol is of the same meaning as defined above].

The compound (I) or a salt thereof can be produced by subjecting the compound represented by the formula (I') to condensation with the compound represented by the formula

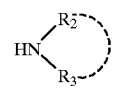

in a solvent, in the presence of a base when necessary, using a condensing agent. Examples of the solvent include hydrocarbons such as benzene, toluene, hexane and heptane, halogenic solvents such as dichloromethane, dichloroethane, chloroform and carbon tetrachloride, ethers such as ethyl ether, tetrahydrofuran and dioxane, acetonitrile and dimethylformamide. As the base, mention is made of triethylamine, 4-dimethylaminopyridine, triethylenediamine and tetramethylethylenediamine. As the condensing agent, mention is made of condensing agents employed for the synthesis of peptide, as exemplified by dicyclohexyl carbodiimide, diethyl cyanophosphate and 1-ethyl-3-(3-dimethylaminopropyl)carbodiimide. The compound represented by the formula

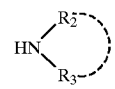

is used in an amount ranging from 0.5 to 2 molar equivalents, preferably from 1 to 1.2 molar equivalent, relative to one mole of the compound shown by the formula (I'), and the condensing agent is used in an amount ranging from 0.5 to 5 molar equivalents, preferably from 1 to 2 molar equivalents. The reaction temperature ranges from 0 to 100°

C., preferably from 20 to 50° C. The reaction time ranges from 0.5 to 24 hours, preferably from about 1 to about 5 hours.

The compound (I) or a salt thereof with X as optionally substituted heterocyclic group having a deprotonizable hydrogen atom, by X, or the carbamoyl group substituted with the optionally substituted heterocyclic group having a deprotonizable hydrogen atom can be produced by converting the carboxyl group in the carbamoyl group substituted with carboxyl group or a substituent having carboxyl group, shown by X, into carboxylic acid amido, subjecting the carboxylic acid amido to dehydration to convert it further into cyano group, then converting the cyano group into the optionally substituted heterocyclic group having a deprotonatable hydrogen atom.

The above-mentioned conversion of carboxylic acid into carboxylic acid amido can be conducted in accordance with a per se known method. For example, a compound with carboxylic acid group is subjected to condensation with ammonium or ammonium chloride, when necessary in the presence of a base (e.g. triethylamine, dimethylaminobenzene, pyridine, potassium carbonate, sodium carbonate, potassium hydrogencarbonate or sodium hydrogencarbonate), using a condensing agent such as diethyl cyanophosphate or dicyclohexyl carboxiimide. As the solvent to be employed, mention is made of ethers such as diethyl ether, tetrahydrofuran or dioxane, halogen type solvents such as dichloromethane, chloroform or carbon tetrachloride, dimethylformamide and acetonitrile. In these solvents, relative to one mole of a compound having carboxyl group, 1 to 100, preferably about 1 to 5, molar equivalent of ammonia or ammonium chloride is used. The reaction temperature ranges from 0 to 100° C., preferably from 0 to 50° C., and the reaction time ranges from 0.1 to 24 hours, preferably from about 0.5 to about 5 hours.

For converting the carboxylic acid amido obtained thus above into cyano group, a compound having carboxylic acid amide is reacted with thionyl chloride in a solvent such as benzene, hexane, toluene or xylene to provide corresponding cyano compound.

The amount of thionyl chloride to be employed ranges, relative to 1 mole of the compound having carboxylic acid amido, from 1 to 10, preferably from 1 to 3, molar equivalents. The reaction temperature ranges from 50 to 200° C., preferably from 70 to 150° C. The reaction time ranges from 0.5 to 10 hours, preferably from about 0.5 to about 3 hours.

The above-mentioned conversion of cyano group into the optionally substituted heterocyclic group having a deprotonizable proton, e.g. tetrazole ring, can be performed by allowing a compound having cyano group to react with trimethylsilyl azide and dibutyltin (IV) oxide in a solvent such as benzene, hexane, toluene or xylene.

The amount of trimethylsilyl azide ranges, relative to 1 mole of the compound having cyano group, from 0.5 to 10, preferably from 1 to 3, molar equivalents, and the amount of dibutyltin (IV) oxide ranges from 0.01 to 3, preferably from about 0.05 to about 1, molar equivalents. The reaction temperature ranges from 0 to 200° C., preferably from 50 to 150° C. The reaction time ranges from 10 to 48 hours, preferably from 15 to 30 hours. Furthermore, conversion into, for example, 2,5-dihydro-5-oxo-1,2,4-oxadiazole ring can be performed by allowing hydroxylamine to react with the compound having cyano group, then by further carbonylating the resultant compound. Hydroxylamine (1 to 10, preferably 1 to 3, equivalents relative to 1 mole of the compound having cyano group) is allowed to react with the compound having cyano group in a solvent as exemplified by an alcohol solvent such as methanol, ethanol and propanol, dimethylformamide or acetonitrile, in the presence of a base such as sodium hydrogencarbonate, potassium hydrogencarbonate or potassium carbonate, at a temperature ranging from 30 to 150° C., preferably from 50 to 100° C., for 1 to 24 hours, preferably about 5 to about 10 hours. For carbonylation of the compound thus obtained, carbodiimide or phosgene, for example, is employed for the carbonylating agent, and, as the solvent, for example, ether type solvents such as diethyl ether, tetrahydrophosgene or dioxane, halogen type solvents such as dichloromethane or chloroform, and ethyl acetate are employed. The amount of the carbonylating agent ranges from 1 to 10, preferably 1 to 3 molar equivalents. The reaction temperature ranges from 30 to 150° C., preferably from 50 to 100° C., and the reaction time ranges from 1 to 24, preferably from about 3 to about 100 hours.

In the above-described reaction, the compound, in which the moiety corresponding to X of the synthetic intermediate is an esterified carboxyl group or an optically active carboxyl group, can be obtained by, for example, the method disclosed in WO095/21834. More specifically, at first, the corresponding racemic compound is obtained, which is then allowed to react with an optically active amino acid to form the amido bond, followed by subjecting the resultant compound to distillation, recrystallization and column chromatography to separate and purify the optically active isomer, and then, the amido bond is again cleaved to give a (3R,5S) compound. Alternatively, by the cleaved reaction step shown by the formula:

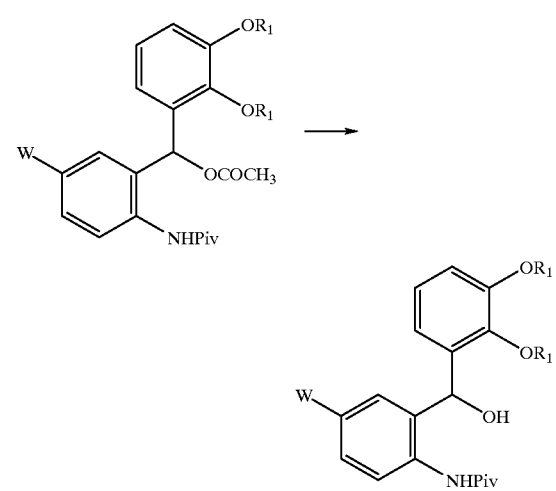

[wherein Piv stands for pivaloyl group, and other symbols are of the same meanings as defined above], enzymatic asymmetric hydrolysis is conducted to give an optically active isomer (S-configuration) of a benzyl alcohol derivative, then, using this optically active isomer as the starting material, in accordance with the method disclosed in EPA567026, to give the above-mentioned (3R,5S) of the compound (I') as defined above.

The compound represented by the formula (I) or a salt thereof in the present invention [hereinafter sometimes called the compound of the formula (I) or the compound (I)] is low in toxicity, has a squalene synthetase inhibiting activity and an activity of lowering the level of triglyceride, and, has an excellent activity of lowering the level of lipids, and is useful for the prophylaxis or therapy of hyperlipemia such as hypercholesteremia and hypertriglycerolemia of mammals (e.g. mouse, rat, rabbit, dog, cat, cow, pig and man), and also useful for the prophylaxis or therapy of renal diseases such as nephritis and nephropathy, arteriosclerosis, ischemic diseases, myocardial infarction, angina pectoris, aneurysm, cerebral arteriosclerosis, peripheral arteriosclerosis, thrombosis, diabetes mellitus (e.g. insulin resistant diabetes), pancreatic disorders and re-stenosis after percutaneous transluminal coronary angioplasty (PTCA).

The use of this invention is described in further detail as follows.

In view of the triglyceride-lowering activity, cholesterol-lowering activity and biological properties of the compound of the formula (1), the compound is especially useful for the therapy and prophylaxis of hyperlipemia, especially hypertriglycerolemia, hyperlipoproteinemia and hypercholesterolemia, and, atherosclerotic diseases caused therefrom, and, secondary diseases thereof, for example, coronary diseases, cerebral ischemia, intermittent claudication and gangrene.

For the therapy of these diseases, the compound of the general formula (1) can be used singly or in combination with any other medicinal ingredients containing a lipid-level lowering agent or a cholestrol-level lowering agent. In this case, these compounds are administered, preferably, orally, and, upon necessity, they may be administered as agents for rectal use in the form of suppository. Examples of medicinal agents which can be used in combination with the compound (I) include fibrates [e.g. chlorofibrate, benzafibrate and gemfibrozil], nicotinic acid, its derivatives and analogues [e.g. acipimox and probucol], bile acid binding resins [e.g. cholestyramine and cholestypol], compounds inhibiting cholesterol absorption [e.g. sitosterol or neomycin], compounds controlling the biosynthesis of cholesterol [e.g. HMG-CoA reductase inhibiting agents such as lovastatin, simvastatin and pravastatin], and squalene epoxidase inhibiting agents [e.g. NB-598 and analogous compounds]. As further agents which can be used in combination with the compound (I), mention is made of, for example, oxidosqualene-lanosterolcyclases such as decalin derivatives, azadecalin derivatives and indane derivatives.

Additional, the compound of the general formula (I) is applicable to treatment of diseases related to hyperchylomicronemia, for example, acute pancreatitis. The mechanism of occurrence of pancreatitis has been considered that minute thrombus occurs in pancreatic blood capillary by the action of chylomicron or by strong topical irritation with the increase of free fatty acid produced by decomposition of triglyceride by pancreatic lipase due to hyperchylomicronemia. In view of the above, since the compound of the formula (I) of this invention has an activity of lowering the level of triglyceride, it can be used for the therapy of pancreatitis, and can be used for the therapy of pancreatitis singly or in combination with a known therapeutic method. For the therapy of this disease, the compound of the formula (I) can be administered orally or topically, or it can be used singly or in combination with a known active compound. As the agent which can be combined for this purpose, mention is made of, for example, aprotinin (trasylol), gabexate mesylate (FOY), nafamostat mesilate (Futhan), citicoline (nicholin) and urinastatin (miraclide). And, for the purpose of removing pain, antichlolinergic drugs, non-narcotic analgesics and narcotic drugs can also be used.

As further noticeable examples of diseases, to which the compound of the general formula (I) is applicable, mention is made of secondary hyperlipemia including, for example, diabetes mellitus, hypothyroidism, nephrotic syndrome or chronic renal failure. In many cases, these diseases cause hyperlipemia and the latter aggravates these diseases, causing a so-called vicious circle. Taking its lipid-level lowering activity into consideration, the compound of the general formula (I) is useful for the therapy and for preventing the aggravation of these diseases. For this purpose, the compound of the general formula (I) can be administered singly or in combination with examplary medicines set forth below.

Medicines for diabetes mellitus: kinedak, benfil, humulin, euglucon, glimicron, daonil, novorin, monotard, insulins, glucobay, dimelin, rastinon, bacilcon, deamiline S, iszilins;

Medicines for hypothyroidism: thyroid (thyreoid), levothyroxine sodium (thyradin S), liothyronine sodium (cylonine, cylomin);

Medicines for nephrotic syndrome: For the therapy using steroid as the first choice, use is made of, for example, predinisolone sodium succinate (predonine), prednisolone sodium succinate (predonine), methyl prednisolone sodium succinate (solu-medrol) and betamethasone (renderon). And, for anticoagulant therapy, use is made of antiplatelet medicines such as dipyridamole (persantine) and dilazep hydrochloride (comelian);

Medicines for chronic renal failure: A combination of diuretics [e.g. furosemide (lasix), bumetanide (lunetoron) and azosemide (diart)], hypotensive drugs (e.g. ACE inhibitors (enalapril maleate (renivace)) and Ca antagonists (Ca antagonistic drugs (maninhilone), α-receptor blocking agents is administered, preferably, orally.

Another possible use of the compound of the general formula (I) of this invention is to inhibit the formation of thrombus. In view of the fact that the triglyceride level in blood is an positive correlation with the blood coagulation factor VII and intake of ω-3 type fatty acid serves to lower the triglyceride level and, at the same time, the coagulation is inhibited, it has been considered that hypertriglycemia would promote the formation of thrombus. Since VLDL (very low density lipoprotein) of the patients suffering from hyperlipemia increased more strongly the secretion of plasminogen activator inhibitor from vascular endothelial cells than that of the patients suffering from normal lipemia, it is considered that triglyceride (hereinafter TG) acts to lower the fibrinolytic activity. Therefore, taking the TG lowering action, the compound of the general formula (I) can be effectively used for the prophylaxis and therapy of the formation of thrombus. The compound (I) can be administered singly or in combination with any of the following exemplary known therapeutic agents, preferably orally.

Medicines for prophylaxis and therapy of thrombus formation: blood coagulation inhibitors [e.g. heparin sodium, heparin calcium, warfarin calcium (warfarin)], thrombolytic agents [e.g. urokinase], antiplatelet agents [e.g. aspirin, sulfinpyrazolo(anturane), dipyridamole (persantine), acropidin (panaldin), cilostazol (pletaal)].

The compound (I) can be used orally or non-orally in the manner of injection, drip infusion, inhalation, rectal administration or topical administration, as it is or as a medicinal composition (e.g. powder, granule, tablet, pill, capsule, injection, syrup, emulsion, elixir, suspension and solution). In other words, at least one species of the compounds of this invention can be used singly or in combination with a pharmaceutically acceptable carrier (e.g. adjuvant, excipient, forming aid and/or diluent).

These pharmaceutical compositions can be prepared by a conventional method. These compositions can be prepared by usually mixing/kneading active components with an additive such as excipients, diluents and carriers. In the present specification, "non-oral administration" include subcutaneous injection, intravenous injection, intramuscular injection, intraperitoneal injection or drip infusion. Injectable compositions, for example, a sterile injectable aqueous suspension or an oily suspension, can be prepared by a known method in the relevant field using a suitable dispersing agent or a moistening agent. The sterile injectable composition may be a solution or a suspension injectable under sterile conditions in a non-toxic diluent or a solvent administrable non-orally, for example, an aqueous solution. As a vehicle or a solvent which can be employed, mention is made of, for example, water, a Ringer solution and an isotonic aqueous saline solution. Further, a sterile non-volatile oil can also be employed as a common solvent or a suspending solvent. For this purpose, any non-volatile oil and fatty acid can also be employed, including natural or synthetic or semi-synthetic fatty oil or fatty acid as well as natural or synthetic or semi-synthetic mono- or di- or triglycerides.

The suppository for rectal use can be prepared by mixing the drug with a suitable non-irritable excipient, e.g. cocoa butter or polyethylene glycol which is solid at normal temperatures, liquid at temperatures in intestinal tube, and melts and release the drug in rectum.

As the solid dosage form for oral administration, mention is made of, for example, powder, granule, tablet, pill and capsule as mentioned above. The composition of such dosage form as above can be prepared by mixing and/or kneading a compound as the active component with at least one species of additives as exemplified by sucrose, lactose, cellulose, mannitol (D-mannitol), multitol, dextrin, starch (e.g. corn starch), microcrystalline cellulose, agar, alginates, chitins, chitosans, pectins, tragacanth gum, acacia, gelatins, collagens, casein, albumin, synthetic or semi-synthetic polymers or glycerides. These compositions may optionally contain further additives, like in usual cases, for example, an inert diluent, a lubricant such as stearic acid and magnesium, a preservative such as parabens and sorbins, an antioxidant such as ascorbic acid, α-tocopherol and cysteine, a disintegrant (e.g. floscaromelose sodium), a binder (e.g. hydroxypropyl cellulose), a thickening agent, a buffering agent, a sweetening agent, a flavoring agent and perfuming agent. Tablets and pills may optionally be prepared with enteric coating. As liquid preparations for oral administration, mention is made of, for example, a pharmaceutically acceptable emulsion, syrup, elixir, suspension and solution, and they may optionally contain an inert diluent such as water and, depending on necessity, an additive. These liquid compositions for oral administration can be prepared by a conventional method, for example, mixing the compound as the active component with an inert diluent and, upon necessity, any other additive.

The orally administrable compositions, while varying with the forms, are incorporated with usually 0.01 to 99 W %, preferably 0.1 to 90 W %, commonly 0.5 to 50% of the compound of this invention as the active component. The dose for a specific patient is determined, while taking into consideration age, body weight, general health conditions, sex, diet, the time of administration, the method of administration, secretion rate, combination of drugs, conditions of the disease then the patient is receiving the therapy and any other factors. A lipid level lowering agent such as a triglyceride level lowering agent comprising the compound (I) of this invention is relatively low in toxicity and can be safely used. Although the daily dose varies depending on the conditions and body weight of the patient, kinds of the compound, administration routes and any other factors, a daily dosage per adult human (about 60 kg body weight) in the case of, for example, oral administration for the prophylaxis and therapy of hyperlipemia ranges from about 1 to 500 mg, preferably from about 10 to 200 mg, of the effective component [compound (I)], and, in the case of a non-orally administrable composition, the daily dose range from about 0.1 to 100 mg, preferably from about 1 to 50 mg, commonly from about 1 to 20 mg in terms of the effective component. Within this range, no toxicity is observed at all.

BEST MODE OF CARRYING OUT THE INVENTION

The following Working Examples, formulation examples and experimental examples are intended to illustrate the present invention in further detail and should by no means be construed as limiting the invention.

EXAMPLES

Working Example 1

Methyl ester of N-[(3R,5S)-7-chloro-5-(2,3-dimethoxyphenyl)-1-neopentyl-2-oxo-1,2,3,5-tetrahydro-4,1-benzoxazepine-3-acetyl]piperidine-4-carboxylic acid

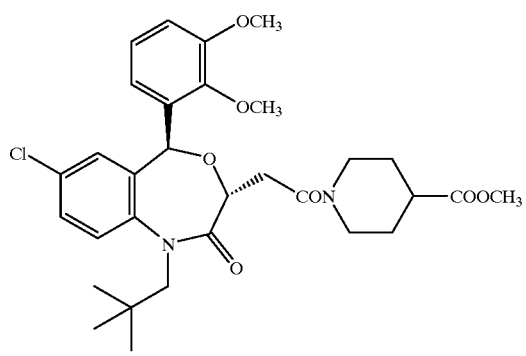

To a solution of (3R,5S)-7-chloro-5-(2,3-dimethoxyphenyl)-1-neopentyl-2-oxo-1,2,3,5-tetrahydro-4, 1-benzoxazepine-3-acetic acid (0.5 g) and 0.25 g of piperidine-4-carboxylic acid methyl ester hydrochloride in dimethylformamide (10 ml) were added, at room temperature, diethylcyanophosphonate (0.28 g) and triethylamine (0.38 ml), and the mixture was stirred for one hour. To the mixture were added water (100 ml) and ethyl acetate (100 ml). The organic layer was washed with 1N HCl and a saturated aqueous solution of sodium hydrogencarbonate, followed by drying over an hydrous magnesium sulfate. The solvent was distilled off, and the residue was purified by silica gel column chromatography (eluents:hexane:ethyl acetate=1:1 (v/v) to afford 0.62 g of a colorless crystalline product, m.p. 124–126° C.

| Elemental analysis for $C_{31}H_{39}ClN_2O_7 \cdot 0.3H_2O$: | |
| --- | --- |
| Calcd.: | C, 62.84; H, 6.74; N, 4.73 |
| Found: | C, 62.78; H, 6.69; N, 4.72 |

Working Example 2

By substantially the same procedure as in Example 1, compounds shown in [Table 1] were obtained.

TABLE 1

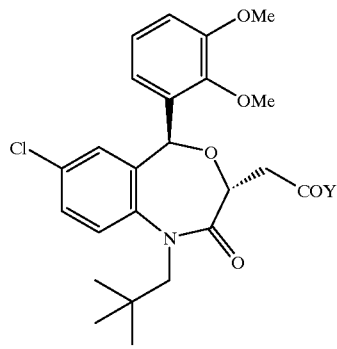

| Compound No. | Y | m.p. (° C.) |
| --- | --- | --- |
| 2-1 | piperazine-N-CH2-CO2Et | 159–160 |
| 2-2 | piperidine-4-CH2-CO2Et | 110–112 |
| 2-3 | NH-CH2-CO2Et | 200–202 |
| 2-4 | NH-CH(CH2OH)-CO2Et | 123–125 |
| 2-5 | H3C-C(OH)(NH-)-CO2Me | 196–198 |
| 2-6 | pyrrolidine-2-CO2Bzl | 169–171 |
| 2-7 | 4-OH-pyrrolidine-2-CO2Me | 256–258 |
| 2-8 | (CH3)2CHCH2-CH(NH-)-CO2Me | 175–177 |
| 2-9 | EtO2C-CH2-CH2-CH(NH-)-CO2Et | 86–89 |
| 2-10 | MeO2C-CH2-CH(NH-)-CO2Me | 154–155 |
| 2-11 | CH3-S-CH2-CH2-CH(NH-)-CO2Me | 141–142 |
| 2-12 | CH3-NH-CH2-CO2Me | 146–148 |

TABLE 1-continued

[Structure: chlorobenzene fused to oxazepine ring with 2,3-dimethoxyphenyl substituent, N-neopentyl, and CH2COY group]

| Compound No. | Y | m.p. (° C.) |
|---|---|---|
| 2-13 | -NH-CH(CH2OH)-CO2Me | 111–113 |
| 2-14 | -NH-CH(CH2CONH2)-COOBzl | 125–127 |
| 2-15 | -NH-CH(Ø)-COOtBu | 180–180.5 |
| 2-16 | -NH-CH(CH2CH2CONH2)-CO2Me | 195–197 |
| 2-17 | -NH-CH(CH(OH)CH3)-CO2Me | 203–204 |
| 2-18 | piperidin-4-ylidene-CH-CO2Me | 132–134 |
| 2-19 | 4-hydroxy-piperidin-4-yl-CO2Me | 197–200 |
| 2-20 | 4-hydroxy-piperidin-4-yl-CH2-CO2Me | 165–166 |
| 2-21 | -NH-CH2CH2-CO2Et | 142–145 |
| 2-22 | trans-4-(NHCH2)-cyclohexyl-CO2Me | 209–210 |

TABLE 1-continued

[Same core structure]

| Compound No. | Y | m.p. (° C.) |
|---|---|---|
| 2-23 | 1-(NH)-cyclohexyl-CO2Me | 123–125 |
| 2-24 | -NH-CH2-CH(OH)-CH2-CO2Me | 96–98 |
| 2-25 | -NH-C6H4-CH2-CO2Me (para) | 107–108 |
| 2-26 | -NH-CH(CH2-C6H4-OH)-CO2Me (tyrosine-like) | 142–144 |
| 2-27 | -NH-CH(CH2-imidazolyl)-CO2Me (histidine-like) | 216–218 |
| 2-28 | -NH-CH(CH2-indolyl)-CO2Me (tryptophan-like) | 132–134 |
| 2-29 | -NH-CH(CH(CH3)2)-CO2tBu | amorphous solid |

TABLE 1-continued

| Compound No. | Y | m.p. (° C.) |
|---|---|---|
| 2-30 | H₃C-CH(CH₃)-CH(NH-)-CO₂Et | amorphous solid |
| 2-31 | piperazinone-N-CH₂-CO₂tBu | amorphous solid |
| 2-32 | 4-piperidinyl-(CH₂)₄-COOEt | 104–106 |
| 2-33 | 4-piperidinyl-(CH₂)₂-COOEt | 115–116 |
| 2-34 | 4-piperidinyl-CH₂-CH=CH-COOEt | 103–105 |
| 2-35 | 4-(OAc)-4-(COOCH₃)-piperidinyl | 193–195 |
| 2-36 | 4-piperidinyl-CH₂-COOCH₃ | 126–128 |
| 2-37 | 4-piperidinyl-CH₂-PO₃Pr^i₂ | 124–127 |
| 2-38 | NH-CH₂-PO₃Et₂ | 150–151 |

Working Example 3

N-[(3R,5S)-7-chloro-5-(2,3-dimethoxyphenyl)-1-neopentyl-2-oxo-1,2,3,5-tetrahydro-4,1-benzoxazepine-3-acetyl]piperidine-4-carboxylic acid

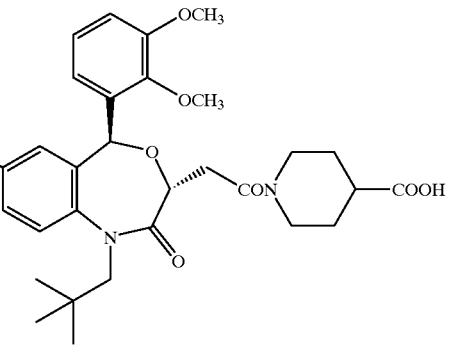

The compound (0.5 g) obtained in Example 1 was dissolved in a mixture of 1N aqueous solution of sodium hydroxide (4 ml), methanol (10 ml) and tetrahydrofuran (5 ml). The solution was stirred for one hour at room temperature, to which were added 1N HCl (50 ml) and ethyl acetate (100 ml). The organic layer was washed with water and dried over anhydrous magnesium sulfate. The solvent was removed, and the residue was recrystallized from hexane-diethyl ether to afford 0.47 g of colorless crystals, m.p. 145–147° C.

Elemental analysis for $C_{30}H_{37}ClN_2O_7 \cdot 0.3H_2O$:

| | |
|---|---|
| Calcd.: | C, 62.29; H, 6.55; N, 4.84 |
| Found: | C, 62.20; H, 6.65; N, 4.83 |

Working Example 4

By subjecting the compound obtained in Example 2 to substantially the same procedure as in Example 3, compounds shown in [Table 2] were obtained.

TABLE 2

| Compound No. | Y | m.p. (° C.) |
|---|---|---|
| 4-1 | N-piperazinyl-CH₂-COOH | amorphous solid |
| 4-2 | 4-piperidinyl-CH₂-COOH | 137–140 |
| 4-3 | NH-CH₂-COOH | 214–217 |
| 4-4 | HOCH₂-CH(NH)-COOH | 132–136 |
| 4-5 | H₃C-CH(OH)-CH(NH)-COOH | 136–144 |
| 4-6 | 2-pyrrolidinyl-COOH | 157–160 |
| 4-7 | 4-hydroxy-2-pyrrolidinyl-COOH | 160–170 |
| 4-8 | (CH₃)(C₂H₅)CH-CH(NH)-COOH | 137–139 |
| 4-9 | HOOC-CH₂-CH(NH)-COOH | 152–155 |
| 4-10 | HOOC-CH₂-CH₂-CH(NH)-COOH | 145–150 |
| 4-11 | CH₃-S-CH₂-CH₂-CH(NH)-COOH | 107–110 |
| 4-12 | CH₃-NH-CH₂-COOH | 134–136 |
| 4-13 | HO-CH₂-CH(NH)-COOH | 135–140 |
| 4-14 | H₂NCO-CH₂-CH(NH)-COOH | 147–150 |

TABLE 2-continued

TABLE 2-continued
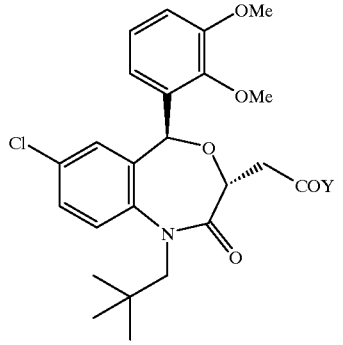
| Compound No. | Y | m.p. (° C.) |
|---|---|---|
| 4-15 | 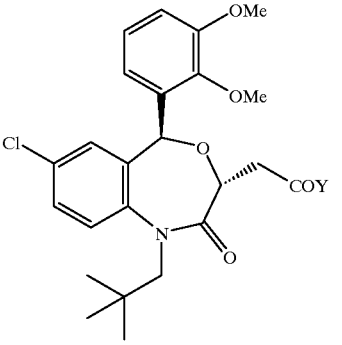 | 134–136 |
| 4-16 | 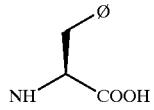 | 140–142 |
| 4-17 | 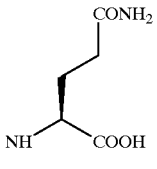 | 137–140 |
| 4-18 | 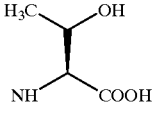 | 228–230 |
| 4-19 | 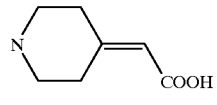 | 156–159 |
| 4-20 | 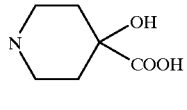 | 163–166 |
| 4-21 | 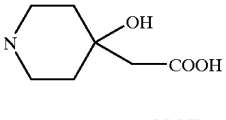 | 165–167 |
| 4-22 |  | 145–147 |
| 4-23 | 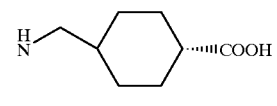 | amorphous solid |
| 4-24 | 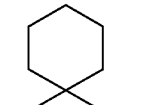 | 122–124 |
TABLE 2-continued
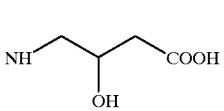
| Compound No. | Y | m.p. (° C.) |
|---|---|---|
| 4-25 | | 158–160 |
| 4-26 | | 160–162 |
| 4-27 | | 200–205 |
| 4-28 | | amorphous solid |
| 4-29 | | 129–132 |
| 4-30 | | 87–92 |
| 4-31 | | 162–164 |

TABLE 2-continued

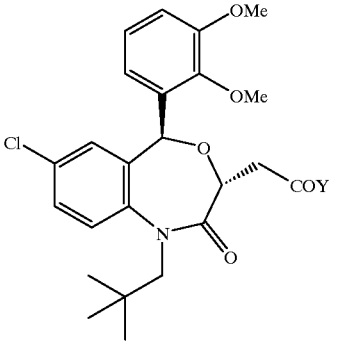

| Compound No. | Y | m.p. (° C.) |
|---|---|---|
| 4-32 | ![piperidine-(CH2)3-COOH] | amorphous solid |
| 4-33 | ![piperidine-(CH2)2-COOH] | 128–131 |
| 4-34 | ![piperidine-CH2-COOH] | 142–145 |

Working Example 5

3-[(3R,5S)-7-Chloro-5-(2,3-dimethoxyphenyl)-1-neopentyl-2-oxo-1,2,3,5-tetrahydro-4,1-benzoxazepine-3-acetamino]propylamine hydrochloride

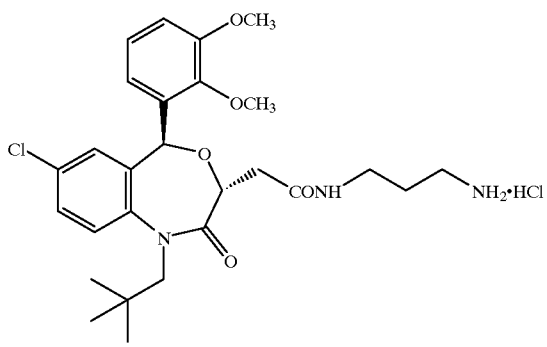

An ethanol solution of the compound (0.2 g) obtained in Example 6-31 and hydrazine-monohydrate (0.10 g) was stirred for one hour at 70° C. To the reaction mixture was added ethyl acetate (50 ml). The mixture was washed with water and dried, followed by distilling off the solvent. The residue was dissolved in acetate (50 ml), to which was added hydrogen chloride (4N solution in ethyl acetate) (0.1 ml). The solvent was distilled off, and the residue was recrystallized from ethanol-diethyl ether to afford 50 mg of colorless crystals, m.p. 158–163° C.

| Elemental analysis for $C_{27}H_{37}Cl_2N_3O_5 \cdot 1.7H_2O$: | |
|---|---|
| Calcd.: | C, 55.42; H, 6.92; N, 7.18 |
| Found: | C, 55.21; H, 6.90; N, 7.12 |

Working Example 6

Employing (3R,5S)-7-chloro-5-(2,3-dimethoxyphenyl)-1-neopentyl-2-oxo-1,2,3,5-tetrahydro-4,1-benzoxazepine-3-acetic acid, substantially the same procedure as in Example 1 was conducted to obtain compounds shown in [Table 3].

TABLE 3

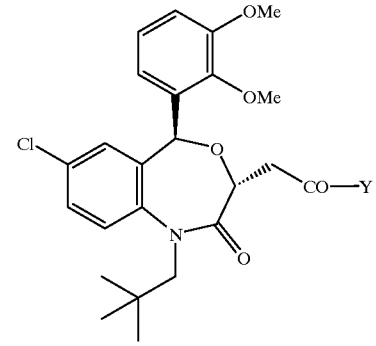

| Compound No. | Y | m.p. (° C.) |
|---|---|---|
| 6-1 | NH-(CH2)2-morpholine | 95–101 |
| 6-2 | NH-(CH2)2-piperidine | 135–230 (decomp.) |
| 6-3 | NH-(CH2)3-piperidine | 101–105 |
| 6-4 | piperidinyl-piperidine · HCl | 270–283 (decomp.) |
| 6-5 | NH-CH2-C6H4-N(CH3)2 | 109–111 |
| 6-6 | piperidinyl-N(CH3)2 | 243–245 |
| 6-7 | NH-(CH2)3-tetrahydroisoquinoline | amorphous solid |

TABLE 3-continued

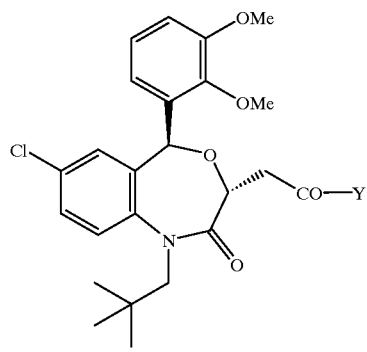

| Compound No. | Y | m.p. (° C.) |
|---|---|---|
| 6-8 | NH-CH₂CH₂-(pyrrolidin-1-yl) | 133–135 |
| 6-9 | NH-(CH₂)₃-morpholin-4-yl | 164–165 |
| 6-10 | NH-(CH₂)₃-pyrrolidin-1-yl | 99–103 |
| 6-11 | NH-CH₂-(pyridin-2-yl) | 96–98 |
| 6-12 | NH-(CH₂)₃-imidazol-1-yl | 143–145 |
| 6-13 | 4-hydroxypiperidin-1-yl | 136–140 |
| 6-14 | (2S)-2-(hydroxymethyl)pyrrolidin-1-yl | 119–122 |
| 6-15 | (2R)-2-(hydroxymethyl)pyrrolidin-1-yl | 119–121 |
| 6-16 | NH-CH(CH₂OH)-CH₂-CH(CH₃)₂ (S) | 106–109 |

TABLE 3-continued

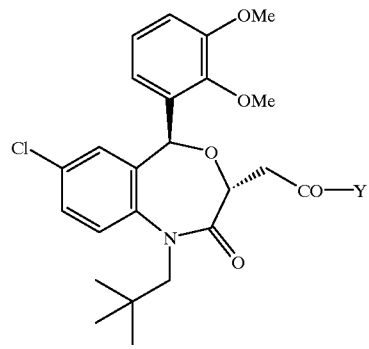

| Compound No. | Y | m.p. (° C.) |
|---|---|---|
| 6-17 | NH-CH(CH₂OH)-CH₂-CH(CH₃)₂ | amorphous solid |
| 6-18 | NH-CH(Ph)-CH₂OH (S) | 204–206 |
| 6-19 | NH-CH(CH(CH₃)₂)-CH₂OH | 106–108 |
| 6-20 | NH-CH(CH₂OH)₂ | 111–121 |
| 6-21 | NH-(CH₂)₃-OH | 118–120 |
| 6-22 | NH-CH₂CH₂-OH | 112–119 |
| 6-23 | NH-CH(CH₂Ph)-CH₂OH (S) | 115–117 |
| 6-24 | NH-CH(CH₃)-CH₂OH (S) | 112–114 |
| 6-25 | 4,4-dimethoxypiperidin-1-yl | 145–148 |
| 6-26 | 1,4-dioxa-8-azaspiro[4.5]decan-8-yl | 184–185 |
| 2-27 | 4-oxopiperidin-1-yl | 125–127 |

TABLE 3-continued

[Structure: chloro-benzoxazepinone with 2,3-dimethoxyphenyl, N-neopentyl, and CH2-CO-Y substituent]

| Compound No. | Y | m.p. (° C.) |
|---|---|---|
| 2-28 | -NH-CH2-C6H4-SO2NH2 | 145–150 |
| 6-29 | piperidin-4-yl (with CN at 4-position), N-linked | 173–174 |
| 6-30 | piperidin-4-yl (with CONH2 at 4-position), N-linked | 181–183 |
| 6-31 | -NH-(CH2)3-phthalimide | oil |
| 6-32 | -NH-(2-isopropyl-6-methylphenyl) | 90–95 |
| 6-33 | -NH-(2,4-difluorophenyl) | 118–120 |
| 6-34 | -NH-CH2-CH=CH2 | 147–148 |
| 6-35 | morpholino (N-linked) | 118–121 |
| 6-36 | piperidino (N-linked) | 97–100 |

TABLE 3-continued

[Same core structure as above]

| Compound No. | Y | m.p. (° C.) |
|---|---|---|
| 6-37 | -N(CH3)2 | 227–228 |
| 6-38 | -NH-CH2-(1H-tetrazol-5-yl) | amorphous solid |
| 6-39 | -NH-(1H-tetrazol-5-yl) | 192–194 |

Working Example 7

(3R,5S)-7-Chloro-5-(2,3-dimethoxyphenyl)-1-neopentyl-1,2,3,5-tetrahydro-3-(1H(or 3H)-tetrazol-5-yl)methyl-4,1-benzoxazepin-2-one

[Structure of the title compound]

(1) A dimethylformamide solution of (3R,5S)-7-chloro-5-(2,3-dimethoxyphenyl)-1-neopentyl-2-oxo-1,2,3,5-tetrahydro-4,1-benzoxazepine-3-acetic acid (2.0 g), ammonium chloride (1.2 g) and triethylamine (1.0 ml) was cooled in ice bath. To the solution were added diethylcyanophosphonate (0.85 g) and triethylamine (0.5 ml). The mixture was stirred for further 20 minutes, to which was added ice-water, followed by extraction with ethyl acetate. The organic layer was washed with water, which was dried over anhydrous magnesium sulfate. The solvent was distilled off, and the residue was recrystallized from diethyl ether to give 1.0 g of (3R,5S)-7-chloro-5-(2,3-dimethoxyphenyl)-1-neopentyl-2-oxo-1,2,3,5- tetrahydro-4,1-benzoxazepine-3-acetamide as colorless crystals, m.p. 170–172° C.

(2) The compound (3.2 g) obtained in (1) and thionyl chloride (1.8 ml) were suspended in toluene (40 ml). The suspension was stirred for one hour at temperatures ranging from 110 to 120° C. The solvent was removed. To the residue were added ethyl acetate (100 ml) and a saturated aqueous solution of sodium hydrogencarbonate (50 ml). The organic layer was dried over anhydrous sodium sulfate, then the solvent was distilled off. The residue was purified by silica gel column chromatography (eluents:hexane:ethyl acetate=3:1 (v/v)) to give 1.7 g of (3R,5S)-7-chloro-5-(2,3-dimethoxyphenyl)-1-neopentyl-1,2,3,5-tetrahydro-3-cyanomethyl-4,1-benzoxazepin-2-one as colorless crystals, m.p. 193–194° C.

(3) To a solution of the compound (1.7 g) obtained in (2) in toluene (20 ml) were added trimethyl silyl azide (0.45 g) and dibutyltin (IV) oxide (30 mg). The mixture was stirred for 24 hours at temperatures ranging from 110 to 120° C. The reaction mixture was concentrated, to which was added diethyl ether (20 ml), followed by washing with an aqueous solution of sodium hydroxide. The aqueous layer was acidified with 1N HCl, which was then subjected to extraction with ethyl acetate. The organic layer was washed with water, which was then dried over anhydrous sodium sulfate. The solvent was distilled off, and the residue was recrystallized from dichloromethane-hexane to give colorless crystals, m.p. 148–150° C.

| Elemental analysis for $C_{24}H_{28}ClN_5O_4 \cdot 0.5H_2O$: | |
| --- | --- |
| Calcd.: | C, 58.24; H, 5.91; N, 14.15 |
| Found: | C, 58.43; H, 6.18; N, 13.76 |

Working Example 8

(3R,5S)-7-Chloro-5-(2,3-dimethoxyphenyl)-1-neopentyl-3-(2,5-dihydro-5-oxo-1,2,4-oxadiazol-3-yl)methyl-1,2,3,5-tetrahydro-4,1-benzoxazepin-2-one

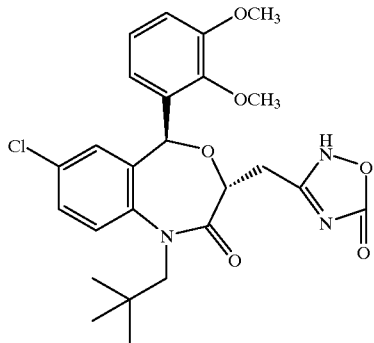

To ethanol (15 ml) were added the compound (0.5 g) obtained in Example 7-(2), hydroxylamine hydrochloride (0.25 g) and sodium carbonate (0.55 g). The mixture was heated for 8 hours under reflux. The reaction mixture was concentrated under reduced pressure, to which were added ethyl acetate (20 ml) and water (20 ml). The organic layer was washed with water, which was then dried over anhydrous sodium sulfate. The solvent was distilled off. The residue (0.55 g), carbodiimidazole (0.5 g) and triethylamine (0.3 ml) were dissolved in ethyl acetate (30 ml). The solution was heated for 6 hours under reflux. The reaction mixture was washed with water and dried. The solvent was distilled off. The residue was purified by silica gel column chromatography (eluents: dichloromethane:methanol:$H_2O$= 250:5:0.5(v/v)) to give 0.44 g of colorless crystals, m.p. 130–133° C.

| Elemental analysis for $C_{25}H_{28}ClN_3O_6$: | |
| --- | --- |
| Calcd.: | C, 59.82; H, 5.62; N, 8.37 |
| Found: | C, 59.57; H, 5.78; N, 7.97 |

Working Example 9

(3R,5S)-7-Chloro-5-(2,3-dimethoxyphenyl)-1-neopentyl-1,2,3,5-tetrahydro-3-(tetrazol-5-yl)methyl-4,1-benzoxazepin-2-one sodium salt

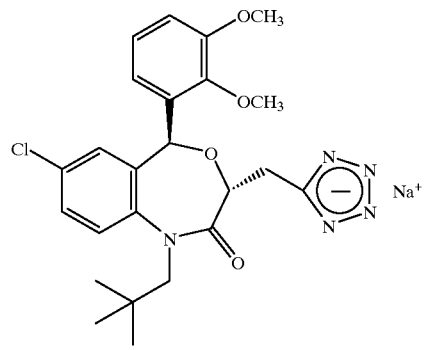

To a solution of the compound (0.6 g) obtained in Example 7 in methanol (10 ml) was added 1N NaOH (1.02 ml), which was concentrated under reduced pressure. The concentrate was dissolved in ethyl acetate (30 ml), which was concentrated under reduced pressure to leave a powdery residue. To the powdery residue was added diethyl ether (20 ml), which was filtrated to collect 0.61 g of a white powdery product.

| Elemental analysis for $C_{24}H_{27}ClN_5O_4Na \cdot H_2O$: | |
| --- | --- |
| Calcd.: | C, 54.81; H, 5.56; N, 13.31 |
| Found: | C, 54.59; H, 5.82; N, 13.03 |

Working Example 10

5-[2-[N-[(3R,5S)-7-Chloro-5-(2,3-dimethoxyphenyl)-1-neopentyl-2-oxo-1,2,3,5-tetrahydro-4,1-benzoxazepine-3-acetyl]piperidin-4-yl]]1H(or 3H)tetrazole

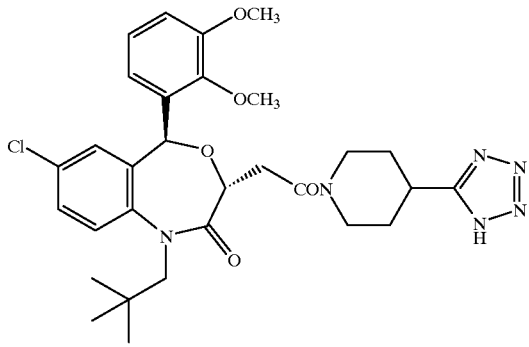

The compound (0.3 g) obtained in Example 6-29 was subjected to substantially the same procedure as in Example 7-(3) to give 0.25 g of colorless crystals, m.p. 185–187° C.

| Elemental analysis for $C_{30}H_{37}ClN_6O_5 \cdot H_2O$: | |
| --- | --- |
| Calcd.: | C, 58.58; H, 6.39; N, 13.66 |
| Found: | C, 58.84; H, 6.15; N, 13.46 |

Working Example 11

(3R,5S)-7-Chloro-5-(2,3-dimethoxyphenyl)-1-(3-hydroxy-2,2-dimethylpropyl)-1,2,3,5-tetrahydro-3-[1H(or 3H)-tetrazol-5-yl]methyl-4,1-benzoxazepin-2-one

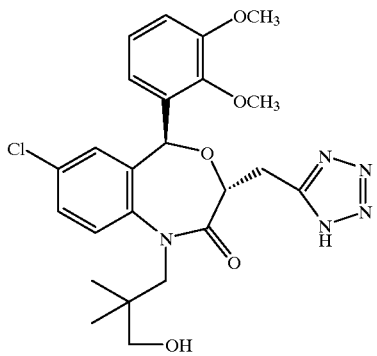

(1) To a solution of (S)-4-chloro-2-[α-hydroxy-(2,3-dimethoxyphenyl)methyl]aniline (2.0 g) and sodium hydrogencarbonate (0.86 g) in ethyl acetate (20 ml) was added dropwise a solution of monoethyl ester of dimethyl malonic acid chloride (1.3 g) in ethyl acetate (20 ml). The mixture was stirred for 3 hours under ice-cooling. To the solution was added water (30 ml), and the organic layer was dried over anhydrous sodium sulfate. The solvent was distilled off, and the residue was purified by silica gel column chromatography to give (S)-2-[N-[2-(2,3-dimethoxy-α-hydroxybenzyl)-4-chlorophenyl]carbamoyl]-2,2-dimethyl acetic acid ethyl ester (2.92 g) as a colorless oily compound.

$^1$H-NMR(CDCl$_3$) δ: 1.22(3H,t,J=7.4 Hz), 1.37(3H,s), 1.42(3H,s), 3.84(3H,s), 3.89(3H,s), 4.05–4.19(3H,m), 6.01 (1H,s), 6.61(1H,dd,J=1.8,7.4 Hz), 6.90–7.05(3H,m), 7.28 (1H,dd,J=3.0,8.8 Hz), 8.07(1H,d,J=8.4 Hz), 9.49(1H,br)

(2) To a solution of the compound (2.83 g) obtained in (1) in tetrahydrofuran (30 ml) was added, under ice-cooling, lithium aluminum hydride (0.5 g). The mixture was stirred for 3 hours at room temperature. To the reaction mixture were added a 1N aqueous solution of sodium hydroxide (13 ml) and water (50 ml), then insolubles were filtered off. The filtrate was extracted with ethyl acetate. The extract was washed with water and dried, then the solvent was distilled off. The residue was purified by silica gel column chromatography (eluents: hexane:ethyl acetate=1:1 (v/v)) to give (S)-[5-chloro-2-(2,2-dimethyl-3-hydroxypropyl)aminophenyl](2,3-dimethoxyphenyl)methanol (0.88 g) as a colorless oily compound.

$^1$H-NMR(CDCl$_3$) δ: 0.91(3H,s), 0.93(3H,s), 2.95(2H,s), 3.37(2H,s), 3.83(3H,s), 3.88(3H,s), 5.99(1H,s), 6.63(1H,d, J=8.8 Hz), 6.77(1H,dd,J=1.6,7.6 Hz), 6.90(1H,dd,J=1.6,7.6 Hz), 7.03(1H,d,J=2.6 Hz), 7.03(1H,t,J=7.6 Hz), 7.13(1H,dd, J=2.6,8.8 Hz)

(3) To a solution of the compound (0.88 g) obtained in (2) in ethyl acetate (10 ml) was added sodium hydrogencarbonate (0.39 g). To the mixture was added a solution of monoethyl ester of fumaric acid chloride (0.45 g) in ethyl acetate (10 ml), which was stirred for 30 minutes at room temperature. The reaction mixture was washed with water and dried, then the solvent was distilled off. The residue was dissolved in ethanol (10 ml), to which was added potassium carbonate (0.70 g). The mixture was stirred overnight at room temperature. To the reaction mixture was added ethyl acetate (50 ml), which was washed with water and dried. The solvent was distilled off, and the residue was recrystallized from ethyl acetate-hexane to give (3R,5S)-7-chloro-5-(2,3-dimethoxyphenyl)-1-(2,2-dimethyl-3-hydroxypropyl)-2-oxo-1,2,3,5-tetrahydro-4,1-benzoxazepine-3-acetic acid ethyl ester (0.57 g) as colorless crystals, m.p. 188–190° C.

(4) The compound (0.5 g) obtained in (3) was dissolved in a mixture of tetrahydrofuran (5 ml) and ethanol (3 ml). To the solution was added a 1N aqueous solution of sodium hydroxide (1 ml), which was stirred for 20 minutes at 60° C. To the reaction mixture was added water (50 ml), which was extracted with ethyl acetate. The extract was dried, and the solvent was distilled off. The residue was recrystallized from ethyl acetate-hexane to give (3R,5S)-7-chloro-5-(2,3-dimethoxyphenyl)-1-(3-hydroxy-2,2-dimethylpropyl)-2-oxo-1,2,3,5-tetrahydro-4,1-benzoxazepine-3-acetic acid (0.33 g) as colorless crystals, m.p. 199–202° C.

(5) To a solution of the compound (2 g) obtained in (4) and 3-aminopropionitrile (0.29 g) in dimethylformamide (20 ml) were added, at room temperature, diethyl cyanophosphonate (0.75 g) and triethylamine (0.51 g). The mixture was stirred for 30 minutes, to which was added ethyl acetate ester (100 ml). The mixture was washed with water and dried. The solvent was then distilled off, and the residue was recrystallized from hexane to give 3-[[(3R,5S)-7-chloro-5-(2,3-dimethoxyphenyl)-1-(3-hydroxy-2,2-dimethylpropyl)-2-oxo-1,2,3,5-tetrahydro-4,1-benzoxazepine-3-acetyl]amino]propionitrile (2.25 g) as colorless crystals, m.p. 118–121° C.

(6) The compound (2 g) obtained in (5) and acetic anhydride (0.39 g) were dissolved in pyridine (20 ml). To the solution was added dimethylaminopyridine (0.1 g), and the mixture was stirred for 30 minutes at room temperature. The solvent was distilled off, and the residue was dissolved in ethyl acetate (100 ml). The solution was washed with 1N HCl and water, followed by drying over anhydrous magnesium sulfate. The solvent was distilled off to leave 3-[(3R,5S)-1-(3-acetyloxy-2,2-dimethylpropyl)-7-chloro-5-(2,3-dimethoxyphenyl)-2-oxo-1,2,3,5-tetrahydro-4,1-benzoxazepine-3-acetyl]aminopropionitrile (2.2 g) as a colorless amorphous solid product.

$^1$H-NMR(CDCl$_3$) δ: 0.95(3H,s), 1.01(3H,s), 2.03(3H,s), 2.55–2.71(2H,m), 2.92(1H,dd,J=8.0,14.4 Hz), 3.41–3.59 (3H,m), 3.62(3H,s), 3.72(1H,d,J=11.2 Hz), 3.86(1H,d,J=11.2 Hz), 3.90(3H,s), 4.33(1H,dd,J=5.0,8.0 Hz), 4.56(1H,d,J=14.2 Hz), 6.26(1H,s), 6.50–6.60(1H,br), 6.64(1H,s), 6.97–7.38(5H,m)

(7) A solution of the compound (2.2 g) obtained in (6), triphenylphosphine (2.0 g), diethyl azodicarboxylate (0.87 g) and triethylsilyl azide (1.3 g) in tetrahydrofuran (10 ml) was stirred for 2 hours at 60° C. The reaction mixture was concentrated under reduced pressure. The concentrate was purified by silica gel column chromatography (eluents: hexane:ethyl acetate=1:1 (v/v)) to give (3R,5S)-7-chloro-3-[1-(2-cyanoethyl)-1H-tetrazol-5-yl]methyl-5-(2,3-dimethoxyphenyl)-1-(2,2-dimethyl-3-hydroxylpropyl)-1,2,3,5-tetrahydro-4,1-benzoxazepin-2-one as a colorless oily compound. This compound was dissolved in a mixture of methanol (10 ml) and tetrahydrofuran (10 ml), to which was added a 1N aqueous solution of sodium hydroxide (8 ml). The mixture was stirred for one hour at 60° C. To the reaction mixture was added water (50 ml), which was acidified with 1N HCl, followed by extraction with ethyl acetate. The extract was dried, and the solvent was distilled off. The residue was recrystallized from ethyl acetate-hexane to give 0.96 g of colorless crystals, m.p. 158–160° C.

| Elemental analysis for C$_{24}$H$_{28}$ClN$_5$O$_5$: | |
|---|---|
| Calcd.: | C, 57.43; H, 5.62; N, 13.95 |
| Found: | C, 57.55; H, 5.58; N, 13.75 |

Working Example 12

The compound obtained in Example 11-(4) was subjected to substantially the same procedure as in Example 1 to afford compounds shown in [Table 4].

TABLE 4

| Compound No. | Y | m.p. (° C.) |
|---|---|---|
| 12-1 | piperidin-4-yl-CH$_2$-COOEt | 115–116 |
| 12-2 | piperidin-4-yl-COOCH$_3$ | 121–124 |
| 12-3 | piperidin-4-ylidene-CH-COOCH$_3$ | 133–135 |
| 12-4 | 4-hydroxy-piperidin-4-yl-COOCH$_3$ | 134–137 |
| 12-5 | 4-hydroxy-piperidin-4-yl-CH$_2$-COOCH$_3$ | 160–161 |
| 12-6 | NH-CH$_2$CH$_2$-pyrrolidin-1-yl | 116–119 |

Working Example 13

The compound obtained in Example 12 was subjected to substantially the same procedure as in Example 3 to afford compounds shown in [Table 5].

TABLE 5

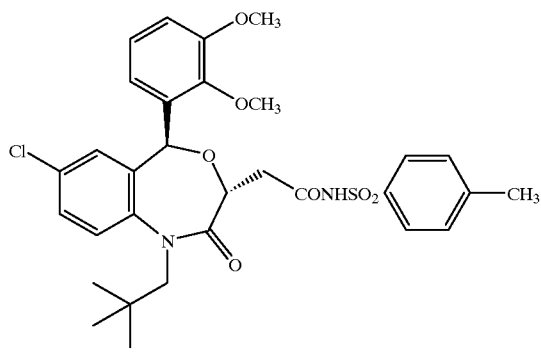

| Compound No. | Y | m.p. (° C.) |
|---|---|---|
| 13-1 | [N-piperidinyl-CH2-COOH] | 135–140 |
| 13-2 | [N-piperidinyl-COOH] | 162–165 |
| 13-3 | [N-piperidinyl=CH-COOH] | 228–230 |
| 13-4 | [N-piperidinyl(OH)-COOH] | 161–165 |
| 13-5 | [N-piperidinyl(OH)-CH2-COOH] | 155–158 |

Working Example 14

N-Toluenesulfonyl-(3R,5S)-7-chloro-5-(2,3-dimethoxyphenyl)-1-neopentyl-2-oxo-1,2,3,5-tetrahydro-4,1-benzoxazepine-3-acetylamide To a solution of (3R,5S)-7-chloro-5-(2,3-dimethoxyphenyl)-1-neopentyl-2-oxo-1,2,3,5-tetrahydro-4,1-benzoxazepine-3-acetic acid (0.5 g) and p-toluenesulfonamide (0.22 g) in dichloromethane were added 1-ethyl-3-(3'-dimethylaminopropyl)carbodiimide (0.27 g) and dimethylaminopyridine (20 mg). The mixture was stirred for 3 hours at room temperature, which was concentrated under reduced pressure. The concentrate was dissolved in ethyl acetate (100 ml). The solution was washed with water and dried, then the solvent was distilled off. The residue was purified by silica gel column chromatography (eluents: dichloromethane:methanol:water=200:10:1 (v/v)) to give 0.6 g of colorless crystals, m.p. 110–113° C.

| Elemental analysis for $C_{31}H_{35}ClN_2O_7S \cdot H_2O$: | |
|---|---|
| Calcd.: | C, 58.81; H, 5.89; N, 4.42 |
| Found: | C, 58.73; H, 5.73; N, 4.62 |

Working Example 15

N-Methylsulfonyl-[N-[(3R,5S)-7-chloro-5-(2,3-dimethoxyphenyl)-1-neopentyl-2-oxo-1,2,3,5-tetrahydro-4,1-benzoxazepine-3-acetyl]piperidine]-4-acetylamide

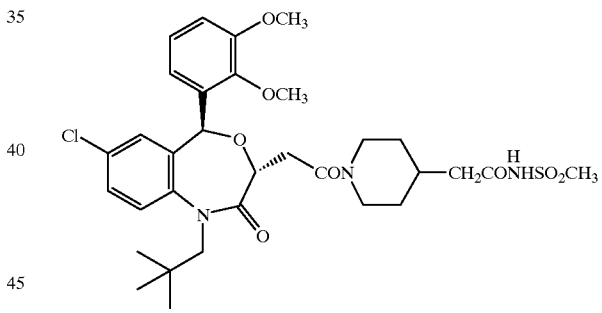

In substantially the same procedure as in Example 14, N-[(3R,5S)-7-chloro-5-(2,3-dimethoxyphenyl)-1-neopentyl-2-oxo-1,2,3,5-tetrahydro-4,1-benzoxazepine-3-acetyl]piperidine-4-acetic acid (0.5 g) obtained in Example 4-2 and methansulfonamide (0.4 g) were used to give 0.3 g of colorless crystals, m.p. 158–160° C.

| Elemental analysis for $C_{32}H_{42}ClN_3O_8S \cdot 0.5H_2O$: | |
|---|---|
| Calcd.: | C, 57.09; H, 6.44; N, 6.24 |
| Found: | C, 56.85; H, 6.47; N, 6.09 |

Working Example 16

N-Methylsulfonyl-(3R,5S)-7-chloro-5-(2,3-dimethoxyphenyl)-1-neopentyl-2-oxo-1,2,3,5-tetrahydro-4,1-benzoxazepine-3-acetylamide

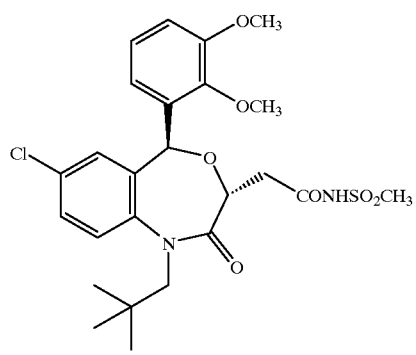

(3R,5S)-7-chloro-5-(2,3-dimethoxyphenyl)-1-neopentyl-2-oxo-1,2,3,5-tetrahydro-4,1-benzoxazepine-3-acetic acid and methansulfonamide were subjected to substantially the same procedure as in Example 14 to afford colorless crystals, m.p. 212° C.

| Elemental analysis for $C_{25}H_{31}ClN_2O_7$: | |
| --- | --- |
| Calcd.: | C, 55.70; H, 5.80; N, 5.20 |
| Found: | C, 55.95; H, 6.01; N, 4.99 |

Working Example 17

By allowing (3R,5S)-7-chloro-5-(2,3-dimethoxyphenyl)-1-neopentyl-2-oxo-1,2,3,5-tetrahydro-4,1-benzoxazepine-3-acetic acid to react respectively with orthomethylphenylsulfonamide, phenylsulfonamide, isopropylsulfonamide and ethylsulfonamide in substantially the same manner as in Working Example 14, the corresponding compounds as shown in Table 6 were produced.

TABLE 6

| Compound No. | R | m.p. (° C.) |
| --- | --- | --- |
| 17-1 | o-tolyl (H3C-phenyl) | amorphous solid |
| 17-2 | phenyl | 158–161 |
| 17-3 | isopropyl (CH(CH3)2) | 149–150 |
| 17-4 | Et | 135–140 |

Working Example 18

N-methylsulfonyl-[N-(3R,5S)-7-chloro-5-(2,3-dimethoxyphenyl)-1-neopentyl-2-oxo-1,2,3,5-tetrahydro-4,1-benzoxazepine-3-acetyl]piperidine]-4-carboxamide Using the compound produced in Working Example 3 (0.5 g) and methanesulfonamide (0.1 g), substantially the same procedure as in Working Example 14 was followed to give 0.41 g of a colorless crystalline product, m.p.187–189° C.

Elemental analysis for $C_{31}H_{40}ClN_3O_8S \cdot 1/2H_2O$:

Calcd.:

C, 56.48; H, 6.27; N, 6.73

Found:

C, 56.28; H, 6.41; N, 6.29

Working Example 19

(3R,5S)-N-methylsulfonyl-7-chloro-5-(2,3-dimethoxyphenyl)-1-(3-hydroxy-2,2-dimethylpropyl)-2-oxo-1,2,3,5-tetrahydro-4,1-benzoxazepine-3-acetamide

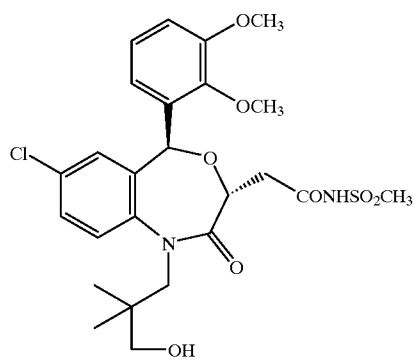

Using the compound produced in Working Example 11-(4) (0.4 g) and methanesulfonamide (0.1 g), substantially the same procedure as in Working Example 14 was followed to give 0.075 g of a colorless crystalline product, m.p.221–223° C.

| Elemental analysis for $C_{25}H_{31}ClN_2O_8S$: | |
|---|---|
| Calcd.: | C, 54.10; H, 5.63; N, 5.05 |
| Found: | C, 54.30; H, 5.69; N, 4.87 |

Working Example 20

(3R,5S)-N-methylsulfonyl-7-chloro-5-(2,3-dimethoxyphenyl)-1-(3-hydroxy-2-hydroxymethyl-2-methylpropyl)-2-oxo-1,2,3,5-tetrahydro-4,1-benzoxazepine-3-acetamide

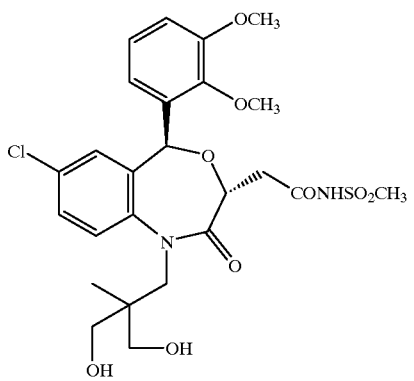

(1) To a solution of oxalyl chloride (2.2 ml) in dichloromethane (120 ml) was added dropwise, at −78° C., a solution of dimethyl sulfoxide (2.4 ml) in dichloromethane (20 ml). The mixture was stirred at −78° C. for 10 minutes, to which was then added a solution of 5-(hydroxymethyl)-2,2,5-trimethyl-1,3-dioxane (2 g) in dichloromethane (40 ml). The mixture was stirred at −78° C. for further 15 minutes. To this solution was added triethylamine (13.2 ml). The mixture was warmed up to 0° C., to which was added a saturated aqueous solution of ammonium chloride (40 ml). The organic layer was washed with water and dried over anhydrous sodium sulfate, followed by distilling off the solvent. The residue was purified by silica gel column chromatography [eluents: hexane-ethyl acetate (3:1)] to give 2 g of aldehyde of a colorless oily compound. To a methanol solution of this aldehyde (2 g) were added (S)-4-chloro-2-[α-hydroxy-(2,3-dimethoxyphenyl)methyl]aniline (3.3 g) and acetic acid (0.75 g). The mixture was stirred at room temperature for 10 minutes, to which was then added sodium cyanoborohydride (0.8 g). The mixture was stirred at 60° C. overnight, to which was added water, followed by extraction with ethyl acetate. The extract was sequentially washed with 1N aqueous solution of sodium hydroxide and water, which was dried over anhydrous sodium sulfate. The solvent was distilled off, and the residue was purified by silica gel column chromatography [eluents: hexane-ethyl acetate (2:1)] to give 3.7 g of (S)-[2-(2,2,5-trimethyl-1,3-dioxan-5-ylmethyl)amino-5-chlorophenyl](2,3-dimethoxyphenyl)methanol as a colorless oily compound.

¹H-NMR(CDCl₃) δ: 0.81(3H,s), 1.38–1.45(6H,m), 3.22 (2H,s), 3.30–3.40(1H,br), 3.60(4H,s), 3.83(3H,s), 3.89(3H, s), 4.90–5.00(4H,br), 5.97(1H,s), 6.71–7.27(6H,m)

(2) To a solution of the compound produced in (1) (3.7 g) in ethyl acetate (40 ml) was added sodium hydrogencarbonate (1.78 g). To the mixture was added, at 0° C., monoethyl ester of fumaric acid chloride (1.41 g). The mixture was stirred at room temperature for 30 minutes. To the solution was added water. The organic layer was washed with water, which was then dried over anhydrous sodium sulfate, followed by distilling off the solvent. The residue (5.2 g) was dissolved in ethanol (100 ml), to which was added potassium carbonate (1.1 g). The mixture was stirred overnight at room temperature. To the reaction mixture was added water, which was extracted with ethyl acetate. The extract was dried over anhydrous sodium sulfate, then the solvent was distilled off. The residue was purified by silica gel column chromatography [eluents: hexane-ethyl acetate (2:1) to ethyl acetate] to afford 2.65 g of (3R,5S)-7-chloro-1-(2,2,5-trimethyl-1,3-dioxan-5-ylmethyl)-5-(2,3-dimethoxyphenyl)-2-oxo-1,2,3,5-tetrahydro-4,1-benzoxazepine-3-acetic acid ethyl ester (A) and 1.12 g of (3R,5S)-7-chloro-1-(3-hydroxy-2-hydroxymethyl-2-methylpropyl)-5-(2,3-dimethoxyphenyl)-2-oxo-1,2,3,5-tetrahydro-4,1-benzoxazepine-3-acetic acid ethyl ester (B), both as colorless amorphous solid products.

A: ¹H-NMR(CDCl₃) δ: 0.95(3H,s), 1.24(3H,t,J=7.0 Hz), 1.36&1.39(each 3H,s), 2.77(1H,dd,J=5.8,16.4 Hz), 3.04(1H, dd,J=7.8,16.4 Hz), 3.29(1H,d,J=12.2 Hz), 3.40(1H,d,J=12.2 Hz), 3.58(3H,s), 3.68(2H,s), 3.89(3H,s), 4.07–4.19(3H,m), 4.40(1H,dd,J=5.8,7.8 Hz), 4.48(1H,d,J=14.2 Hz), 6.16(1H, s), 6.63(1H,d,J=1.8 Hz), 6.95–7.45(6H,m)

B: ¹H-NMR(CDCl₃) δ: 0.62(3H,s), 1.25(3H,t,J=7.0 Hz), 2.78(1H,dd,J=5.2,16.6 Hz), 3.07(1H,dd,J=8.2,16.6 Hz), 3.39–3.80(4H,m), 3.60(3H,s), 3.89(3H,s), 4.13(2H,dq,J= 1.8,7.0 Hz), 4.20–4.28(1H,m), 4.41(1H,dd,J=5.2,18.2 Hz), 4.85(1H,d,J=14.6 Hz), 6.12(1H,s), 6.63(1H,s), 6.89–7.39 (6H,m)

(3) To an ethanol solution of the compound (A) produced in (2) (2.25 g) was added a 1N aqueous solution of sodium hydroxide (4.0 ml). The mixture was stirred at 60° C. for one hour, to which was added water, followed by neutralization with 1N HCl. The reaction mixture was extracted with ethyl acetate. The extract was dried over anhydrous sodium sulfate, then the solvent was distilled off to leave 2.3 g of (3R,5S)-7-chloro-1-(2,2,5-trimethyl-1,3-dioxan-5-ylmethyl)-5-(2,3-dimethoxyphenyl)-2-oxo-1,2,3,5-tetrahydro-4,1-benzoxazepine-3-acetic acid as a colorless amorphous solid product.

¹H-NMR(CDCl₃) δ: 0.95(3H,s), 1.35&1.39(each 3H,s), 2.84(1H,dd,J=5.4,16.4 Hz), 3.08(1H,dd,J=7.8,16.4 Hz), 3.28(1H,d,J=12.2 Hz), 3.41(1H,d,J=12.2 Hz), 3.58(3H,s), 3.69(2H,s), 3.89(3H,s), 4.16(1H,d,J=13.8 Hz), 4.35(1H,dd, J=5.4,7.8 Hz), 4.89(1H,d,J=13.8 Hz), 6.16(1H,s), 6.65(1H, d,J=2.0 Hz), 6.96–7.47(5H,m)

(4) To a solution of the compound produced in (3) (0.15 g) in dimethylformamide (2 ml) were added methanesulfonamide (29 mg), 1-ethyl-3-(3-dimethylaminopropyl) carbodiimide.hydrochloride (65 mg) and dimethylaminopyridine (10 mg). The mixture was stirred overnight at room temperature, to which was added ethyl acetate (50 ml). The mixture was washed with water, followed by drying over anhydrous sodium sulfate. The solvent was distilled off, and the residue was dissolved in acetone (2 ml). To the solution was added p-toluenesulfonic acid monohydrate (0.1 g). The mixture was stirred overnight at room temperature, to which was added ethyl acetate (50 ml). The mixture was washed with water, which was dried over anhydrous sodium sulfate, followed by distilling off the solvent. The residue was washed with a mixture of ethyl ether and hexane (1:1), which was filtrated to afford 40 mg of a colorless amorphous solid product.

¹H-NMR(CDCl₃) δ: 0.63(3H,s), 2.85–2.92(2H,m), 3.28 (3H,s), 3.25–3.70(5H,m), 3.59(3H,s), 3.89(3H,s), 4.43(1H, t,J=6.1 Hz), 4.78(1H,d,J=14.2 Hz), 8.16(1H,s), 6.67(1H,s), 6.95–7.40(6H,m)

Working Example 21

N-methylsulfonyl-[N-[(3R,5S)-7-chloro-5-(2,3-dimethoxyphenyl)-1-(3-hydroxy-2,2-dimethylpropyl)-2-oxo-1,2,3,5-tetrahydro-4,1-benzoxazepine-3-acetyl]piperidine]-4-acetamide

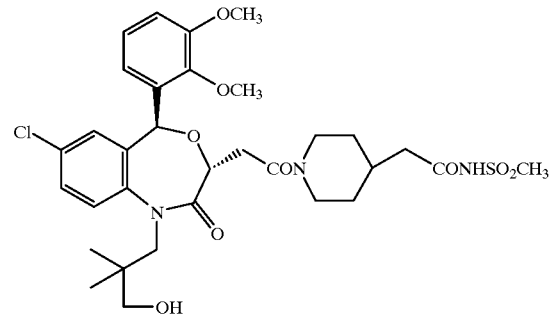

Using the compound (0.5 g) produced in Working Example 13-1 and methanesulfonamide (0.1 g), substantially the same procedure as in Working Example 14 was followed to give 90 mg of colorless crystals, m.p.175–180° C.

| Elemental analysis for $C_{32}H_{42}ClN_3O_9S$: | |
|---|---|
| Calcd.: | C, 56.50; H, 6.22; N, 6.18 |
| Found: | C, 56.70; H, 6.50; N, 5.90 |

Working Example 22

(3R,5S)-N-phosphonomethyl-7-chloro-5-(2,3-dimethoxyphenyl)-1-neopentyl-2-oxo-1,2,3,5-tetrahydro-4,1-benzoxazepine-3-acetamide

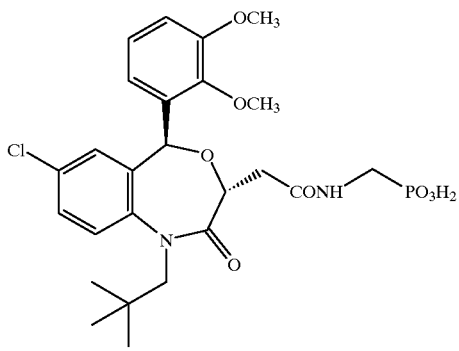

To a solution of the compound (1.0 g) produced in Working Example 2-38 in dichloromethane (5 ml) was added trimethylsilyl bromide (0.38 g). The mixture was stirred overnight at room temperature, to which was added ethyl acetate. The mixture was washed with a 0.5N aqueous solution of sodium hydroxide, a saturated aqueous solution of ammonium chloride and water, followed by drying over anhydrous sodium sulfate. The solvent was distilled off, and the residue was recrystallized from a mixture of ethanol and diethyl ether (1:10) to afford 0.41 g of colorless crystals, m.p.152–155° C.

| Elemental analysis for $C_{25}H_{32}ClN_2O_8P \cdot 1.7H_2O$: | |
|---|---|
| Calcd.: | C, 51.28; H, 6.09; N, 4.78 |
| Found: | C, 51.20; H, 6.11; N, 4.77 |

Working Example 23

N-[(3R,5S)-7-chloro-5-(2,3-dimethoxyphenyl)-1-neopentyl-2-oxo-1,2,3,5-tetrahydro-4,1-benzoxazepine-3-acetyl]-4-phosphonomethylpiperidine

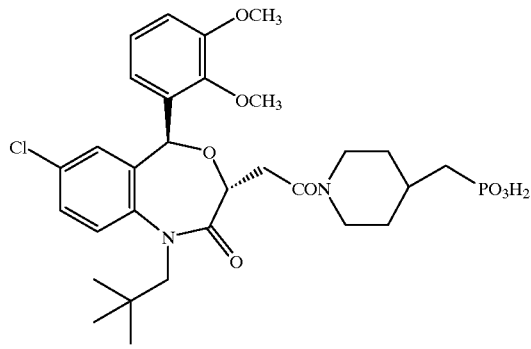

Using the compound produced in Working Example 2-37 (2 g), substantially the same procedure as in Working Example 22 was followed to afford 1 g of colorless crystals, m.p.174–175° C.

| Elemental analysis for $C_{30}H_{41}ClN_2O_8P$: | |
|---|---|
| Calcd.: | C, 56.12; H, 6.75; N, 4.36 |
| Found: | C, 55.95; H, 6.58; N, 4.05 |

Working Example 24

5-[[N-[(3R,5S)-7-chloro-5-(2,3-dimethoxyphenyl)-1-neopentyl-2-oxo-1,2,3,5-tetrahydro-4,1-benzoxazepine-3-acetyl]piperidin-4-yl]methyl]1H(or 3H)-tetrazole

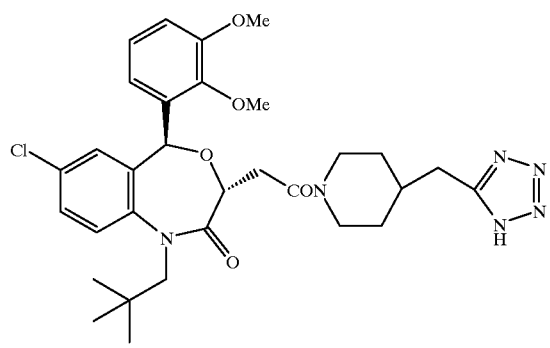

(1) To a solution of the compound produced in Working Example 4-2 (1.5 g) and ammonium chloride (0.7 g) in dimethylformamide (12 ml) were added, at 0° C., triethylamine (2.0 ml) and diethyl cyanophosphonate (0.5 g). The mixture was stirred for 40 minutes, to which was added water. The mixture was extracted with ethyl acetate. The extract solution was washed with water and dried over anhydrous sodium sulfate, followed by distilling off the solvent. The residue was recrystallized from hexane-ethyl acetate to afford 1.3 g of an amide compound, m.p.189–190° C.

(2) To a suspension of the compound produced in (1) (1.0 g) in toluene (20 ml) was added thionyl chloride (1 ml). The mixture was stirred at 90° C. for 30 minutes. To the reaction mixture was added a saturated aqueous solution of sodium hydrogen carbonate. The mixture was to extracted with ethyl acetate. The organic layer was dried, then the solvent was distilled off. The residue was purified by silica gel column chromatography [eluents: hexane-ethyl acetate-methanol (15:10:1)] to give 0.69 g of colorless crystals, m.p.150–152° C.

(3) Using the compound produced in (2) (0.4 g), trimethylsilyl azide (0.16 g) and dibutyltin (IV) oxide (20 mg), substantially the same procedure as in Working Example 7-(3) was followed to afford 0.37 g of colorless crystals, m.p.168–170° C.

| Elemental analysis for $C_{31}H_{39}ClN_6O_5 \cdot H_2O$: | |
|---|---|
| Calcd.: | C, 59.18; H, 6.58; N, 13.36 |
| Found: | C, 59.16; H, 6.43; N, 13.03 |

Working Example 25

5-[2-[N-[(3R,5S)-7-chloro-5-(2,3-dimethoxyphenyl)-1-neopentyl-2-oxo-1,2,3,5-tetrahydro-4,1-benzoxazepine-3-acetyl]piperidin-4-yl]ethyl]1H(or 3H)-tetrazole

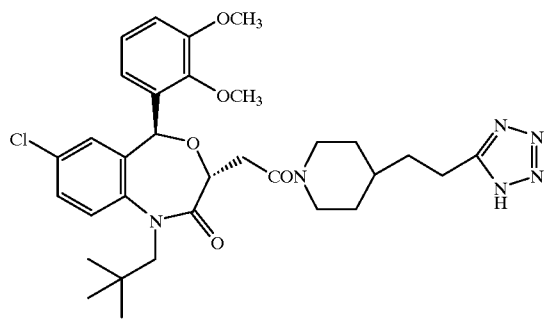

The compound produced in Working Example 4-34 (0.3 g) was subjected to substantially the same procedure as in Working Example 24 to afford 0.25 g of colorless crystals, m.p.155–158° C.

| Elemental analysis for $C_{32}H_{41}ClN_6O_5 \cdot H_2O$: | |
|---|---|
| Calcd.: | C, 59.76; H, 6.74; N, 13.07 |
| Found: | C, 59.91; H, 6.75; N, 12.87 |

Working Example 26

(3R,5S)-N-bis(ethoxy)phosphinylmethyl-7-chloro-5-(2,3-dimethoxyphenyl)-1-(3-hydroxy-2,2-dimethylpropyl)-2-oxo-1,2,3,5-tetrahydro-4,1-benzoxazepine-3-acetamide

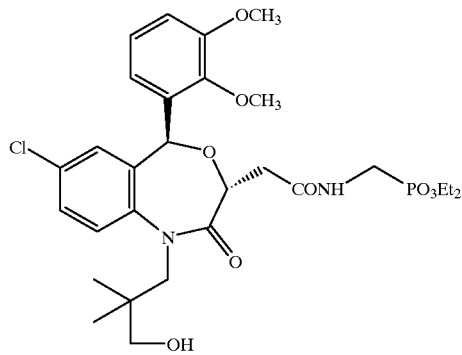

Using the compound produced in Working Example 11-(4) (1.0 g) and diethyl aminomethylphosphonate (0.38 g), substantially the same procedure as in Working Example 1 was followed to afford 1.24 g of colorless crystals, m.p.138–140° C.

| Elemental analysis for $C_{29}H_{40}ClN_2O_9P$: | |
|---|---|
| Calcd.: | C, 55.55; H, 6.43; N, 4.47 |
| Found: | C, 55.25; H, 6.47; N, 4.44 |

Working Example 27

(3R,5S)-N-phosphonomethyl-7-chloro-5-(2,3-dimethoxyphenyl)-1-(3-hydroxy-2,2-dimethylpropyl)-2-oxo-1,2,3,5-tetrahydro-4,1-benzoxazepine-3-acetamide

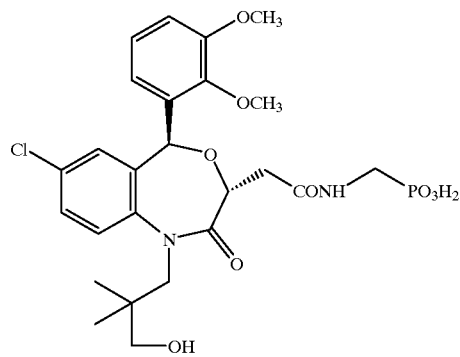

The compound produced in Working Example 26 (0.3 g) was subjected to substantially the same procedure as in Working Example 22 to afford 0.26 g of an amorphous solid compound.

$^1$H-NMR(CD$_3$OD) δ: 0.84(3H,s), 0.93(3H,s), 2.75–2.82 (2H,m), 3.20(1H,d,J=11.4 Hz), 3.40–3.70(3H,m), 3.58(3H, s), 3.89(3H,s), 4.35–4.46(2H,m), 6.18(1H,s), 6.53(1H,d,J= 2.2 Hz), 7.08–7.61(5H,m)

Working Example 28

Bispivaloyloxymethyl N-[(3R,5S)-7-chloro-5-(2,3-dimethoxyphenyl)-1-neopentyl-2-oxo-1,2,3,5-tetrahydro-4,1-benzoxazepin-3-yl]-4-bis(pivaloyloxymethyl)phosphinylmethylpiperidine

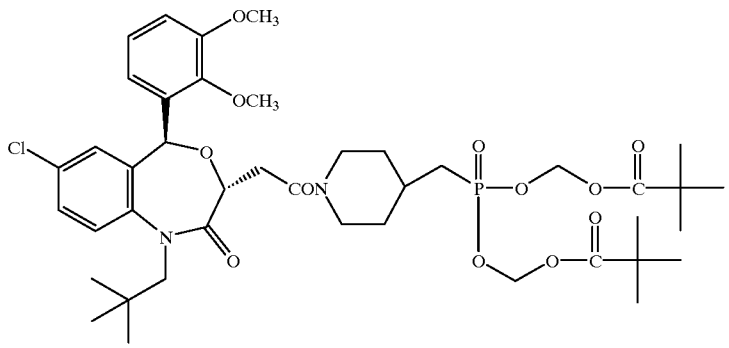

To a solution of the compound produced in Working Example 23 (0.15 g) and potassium hydroxide (28.2 mg) in water (1.5 ml) was added a solution of silver nitrate (102 mg). The mixture was stirred for 15 minutes, then resulting insolubles were collected by filtration, washed with water and diethyl ether, followed by drying under reduced pressure. The solid matter thus obtained was suspended in dichloromethane (2 ml). To the suspension was added Molecular Sieves (3A) (200 mg), and the mixture was stirred for 40 minutes. To the reaction mixture were added anisole (0.1 g) and pivaloylmethyl iodide (0.27 g), which was stirred at room temperature for 40 minutes, followed by filtering off insolubles. To the filtrate was added ethyl acetate (50 ml). The mixture was washed with water and dried, followed by distilling off the solvent. The residue was purified by silica gel column chromatography [eluents: hexane-ethyl acetate (1:1)] to afford 56 mg of a colorless amorphous solid product.

$^1$H-NMR(CDCl$_3$) δ: 0.94(9H,s), 1.23(18H,s), 1.50–1.95 (7H,m), 2.54–2.75(2H,m), 2.97–3.18(2H,m), 3.37(1H,d,J= 14.4 Hz), 3.62(3H,s), 3.89(3H,s), 3.90–4.00(1H,m), 4.48–4.54(3H,m), 5.64(2H,s), 5.70(2H,s), 6.27(1H,s), 6.59 (1H,s), 6.95(1H,s), 6.95–7.33(5H,m)

Working Example 29

N-[(3R,5S)-7-chloro-1-(2,2,5-trimethyl-1,3-dioxan-5-ylmethyl)-5-(2,3-dimethoxyphenyl)-2-oxo-1,2,3,5-tetrahydro-4,1-benzoxazepine-3-acetyl]piperidine-4-acetic acid ethyl ester

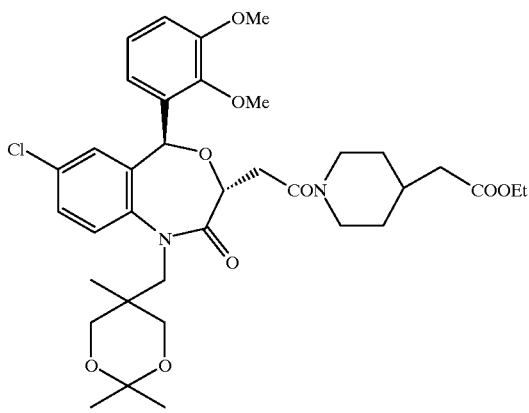

Using the compound produced in Working Example 20-(3) (2 g) and piperidine-4-acetic acid ethyl ester hydrochloride (0.7 g), substantially the same procedure as in Working Example 1 was followed to afford 2.4 g of a colorless amorphous solid product.

$^1$H-NMR(CDCl$_3$) δ: 0.96(3H,s), 1.25(3H,t,J=7.2 Hz), 1.36&1.39(each 3H,s), 1.65–1.82(4H,m), 1.95–2.08(1H,m), 2.18–2.26(2H,m), 2.49–2.63(1H,m), 2.73(1H,dd,J=4.8,15.8 Hz), 2.92–3.06(1H,m), 3.12(1H,dd,J=8.2,15.8 Hz), 3.31 (1H,d,J=12.0 Hz), 3.10(1H,d,J=12.0 Hz), 3.58(3H,s), 3.65 (1H,d,J=11.8 Hz), 3.73(1H,d,J=11.8 Hz), 3.89(3H,s), 3.94–3.99(1H,m), 4.04–4.18(3H,m), 4.46–4.56(3H,m), 6.16 (1H,s), 6.60–6.62(1H,m), 6.95–7.46(5H,m)

Working Example 30

N-[(3R,5S)-7-chloro-1-(3-hydroxy-2-hydroxymethyl-2-methylpropyl)-5-(2,3-dimethoxyphenyl)-2-oxo-1,2,3,5-tetrahydro-4,1-benzoxazepine-3-acetyl]piperidine-4-acetic acid ethyl ester

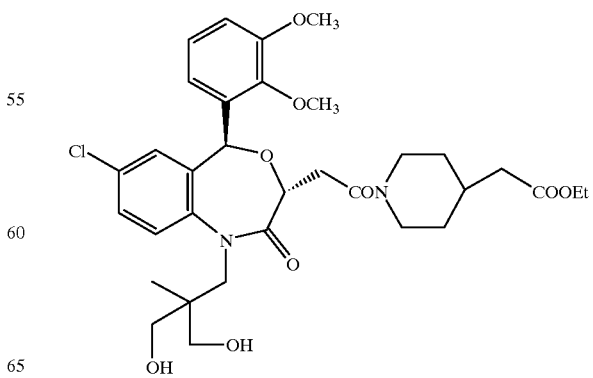

To a solution of the compound produced in Working Example 29 (2.0 g) in acetone (20 ml) were added p-toluenesulfonic acid monohydrate (35 mg) and water (2 ml). The mixture was stirred at 50° C. for 6 hours. To the reaction mixture was added ethyl acetate (50 ml). The mixture was washed with a 1N aqueous solution of sodium hydroxide and water, followed by drying over anhydrous sodium sulfate. The solvent was distilled off to leave 1.62 g of a colorless amorphous solid product.

$^1$H-NMR(CDCl$_3$) δ: 0.62(3H,s), 1.00–1.34(2H,m), 1.26 (3H,t,J=7.4 Hz), 1.70–1.81(2H,m), 1.95–2.08(1H,m), 2.19–2.28(2H,m), 2.51–2.78(2H,m), 3.01–3.08(1H,m), 3.17 (1H,dd,J=9.0,15.2 Hz), 3.40–3.74(5H,m), 3.60(3H,s), 3.89 (3H,s), 3.89–3.94(1H,m), 4.13(2H,q,J=7.4 Hz), 4.48–4.54 (2H,m), 4.83(1H,d,J=14.6 Hz), 6.13(1H,s), 6.61(1H,d,J=1.8 Hz), 6.97–7.44(5H,m)

Working Example 31

N-[(3R,5S)-7-chloro-1-(3-hydroxy-2-hydroxymethyl-2-methylpropyl)-5-(2,3-dimethoxyphenyl)-2-oxo-1,2,3,5-tetrahydro-4,1-benzoxazepine-3-acetyl]piperidine-4-acetic acid

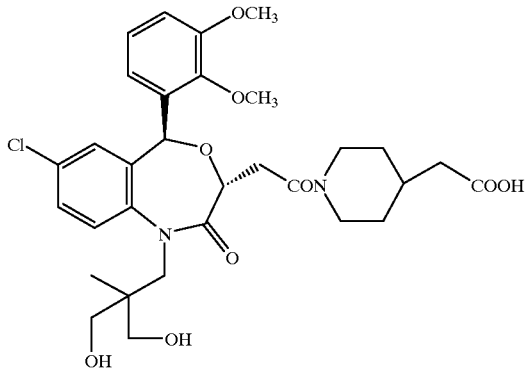

To an ethanol solution of the compound produced in Working Example 30 was added a 1N aqueous solution of sodium hydroxide. The mixture was stirred at 60° C. for 2 hours. To the reaction mixture were added water (100 ml) and ethyl acetate (50 ml), which was acidified with 1N HCl.

The organic layer was washed with water and dried over anhydrous sodium sulfate. The solvent was distilled off to leave 0.94 g of a colorless amorphous solid product.

$^1$H-NMR(CDCl$_3$) δ: 0.63(3H,s), 1.05–1.36(2H,m), 1.70–1.85(2H,m), 1.92–2.05(1H,m), 2.23–2.32(2H,m), 2.51–2.80(2H,m), 2.96–3.23(2H,m), 3.44–3.70(5H,m), 3.60 (3H,s), 3.89(3H,s), 3.91–4.00(1H,m), 4.48–4.54(2H,m), 4.78(1H,d,J=15.2 Hz), 6.12(1H,s), 6.61(1H,s), 6.97–7.39 (5H,m)

Working Example 32

N-[(3R,5S)-1-(3-acetoxy-2-acetoxymethyl-2-methylpropyl)-7-chloro-5-(2,3-dimethoxyphenyl)-2-oxo-1,2,3,5-tetrahydro-4,1-benzoxazepine-3-acetyl]piperidine-4-acetic acid ethyl ester

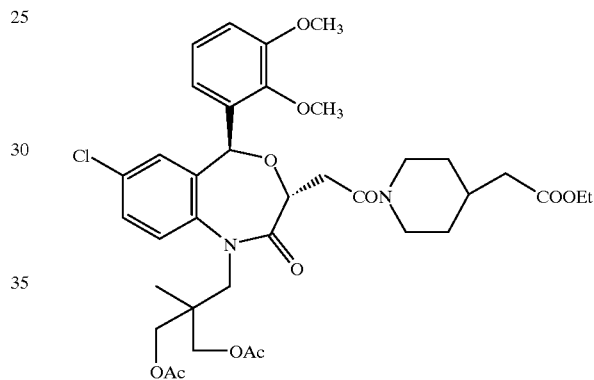

To a solution of the compound produced in Working Example 30 (0.5 g) in pyridine (5 ml) were added acetic anhydride (0.20 g) and dimethylaminopyridine (10 mg). The mixture was stirred at room temperature for 30 minutes. To the reaction mixture was added ethyl acetate (50 ml). The mixture was washed with 1N HCl and water, which was then dried, followed by distilling off the solvent. The residue was purified by silica gel column chromatography (eluents: ethyl acetate) to afford 0.50 g of a colorless amorphous solid product.

$^1$H-NMR(CDCl$_3$) δ: 1.02(3H,s), 1.00–1.40(2H,m), 1.25&1.26(total 3H, each t, J=7.2 Hz), 1.60–1.80(2H,m), 1.92–2.05(1H,m), 2.00(3H,s), 2.03(3H,s), 2.16–2.26(2H,m), 2.46–2.65(1H,m), 2.67–2.77(1H,m), 2.99–3.19(2H,m), 3.60 (3H,s), 3.64–4.19(6H,m), 3.89(3H,s), 4.44–4.54(2H,m), 4.67(1H,d,J=14.6 Hz), 6.23(1H,s), 6.65(1H,s), 6.96–7.34 (5H,m)

Working Example 33

N-[(3R,5S)-1-(3-acetoxy-2-acetoxymethyl-2-methylpropyl)-7-chloro-5-(2,3-dimethoxyphenyl)-2-oxo-1,2,3,5-tetrahydro-4,1-benzoxazepine-3-acetyl]piperidine-4-acetic acid

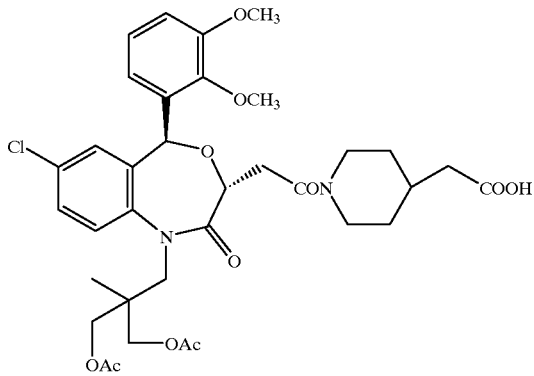

Using the compound produced in Working Example 31, substantially the same procedure as in Working Example 32 was followed to afford 0.28 g of a colorless amorphous solid product.

$^1$H-NMR(CDCl$_3$) δ: 0.95–1.36(2H,m), 1.03(3H,s), 1.71–1.83(2H,m), 1.93–2.07(1H,m), 2.00(3H,s), 2.05(3H,s), 2.23–2.33(2H,m), 2.48–2.63(1H,m), 2.65–2.78(1H,m), 3.00–3.18(2H,m), 3.60(3H,s), 3.65–4.14(6H,m), 3.89(3H,s), 4.46–4.56(2H,m), 4.66(1H,d,J=14.8 Hz), 6.24(1H,s), 6.64 (1H,s), 6.96–7.34(5H,m)

Working Example 34

(3R,5S)-N-methylsulfonyl-1-(3-acetoxy-2-acetoxymethyl-2-methylpropyl)-7-chloro-5-(2,3-dimethoxyphenyl)-2-oxo-1,2,3,5-tetrahydro-4,1-benzoxazepine-3-acetamide

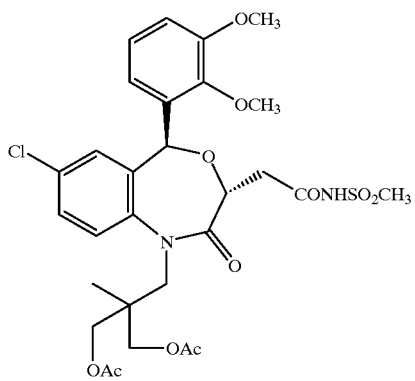

Using the compound produced in Working Example 20 (0.1 g), acetic anhydride (39 mg) and dimethylaminopyridine (5 mg), substantially the same procedure as in Working Example 32 was followed to afford 70 mg of a colorless amorphous solid product.

$^1$H-NMR(CDCl$_3$) δ: 1.00(3H,s), 2.00&2.02(each 3H,s), 2.85(1H,dd,J=5.4,15.4 Hz), 2.98(1H,dd,J=7.2,15.4 Hz), 3.26(3H,s), 3.61(3H,s), 3.70(1H,d,J=14.2 Hz), 3.84(1H,d,J= 11.4 Hz), 3.89(3H,s), 3.94–3.99(2H,m), 4.11(1H,d,J=11.4 Hz), 4.40(1H,d,J=6.2 Hz), 4.46(1H,d,J=14.2 Hz), 6.28(1H, s), 6.69(1H,d,J=1.6 Hz), 6.97–7.43(5H,m)

Working Example 35

N-[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepine-3-acetyl]piperidine-4-acetic acid ethyl ester

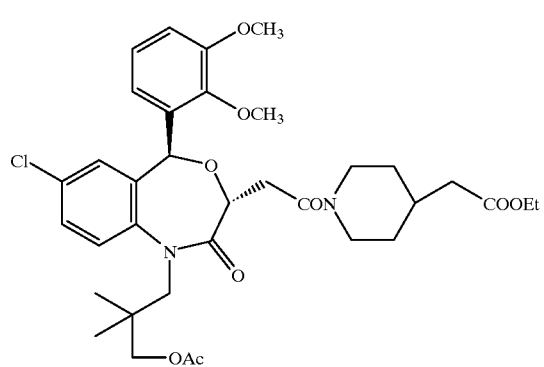

Using the compound produced in Working Example 12-1 (0.5 g), substantially the same procedure as in Working Example 32 was followed to afford 0.35 g of a colorless amorphous solid product.

$^1$H-NMR(CDCl$_3$) δ: 0.93(3H,s), 1.02(3H,s), 1.26(3H,t), 2.02(3H,s), 3.61(3H,s), 3.89(3H,s), 4.14(2H,q), 4.5(3H,m), 6.26(1H,s), 6.62(1H,s), 6.9–7.4(5H,m)

Working Example 36

N-[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepine-3-acetyl]piperidine-4-acetic acid Using the compound produced in Working Example 13-1 (0.37 g), substantially the same procedure as in Working Example 32 was followed to afford 0.35 g of a colorless crystalline product, m.p.194–196° C.

| Elemental analysis for $C_{33}H_{41}ClN_2O_9$: | |
|---|---|
| Calcd.: | C, 61.44; H, 6.41; N, 4.34 |
| Found: | C, 61.23; H, 6.18; N, 4.39 |

Working Example 37

N-[(3R,5S)-7-chloro-1-(3-hydroxy-2-hydroxymethyl-2-methylpropyl)-5-(2,3-dimethoxyphenyl)-2-oxo-1,2,3,5-tetrahydro-4,1-benzoxazepine-3-acetyl]-4-hydroxypiperidine-4-acetic acid methyl ester

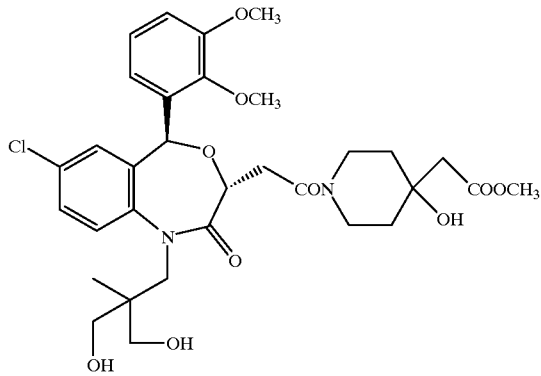

(1) To a solution of (3R,5S)-7-chloro-1-(3-hydroxy-2-hydroxymethyl-2-methylpropyl)-5-(2,3-dimethoxyphenyl)-2-oxo-1,2,3,5-tetrahydro-4,1-benzoxazepine-3-acetic acid ethyl ester (1.0 g) in ethanol (10 ml) was added a 1N aqueous solution of sodium hydroxide. The mixture was stirred at 60° C. for one hour. To the reaction mixture was added water, which was neutralized with 1N HCl, followed by subjecting to extraction with ethyl acetate. The extract solution was dried over anhydrous sodium sulfate. The solvent was distilled off, and the residue was recrystallized from a mixture of ethyl acetate and hexane to afford 0.38 g of (3R,5S)-7-chloro-1-(3-hydroxy-2-hydroxymethyl-2-methylpropyl)-5-(2,3-dimethoxyphenyl)-2-oxo-1,2,3,5-tetrahydro-4,1-benzoxazepine-3-acetic acid, m.p.208–210° C.

(2) Using the compound produced in (1) (0.25 g) and 4-hydroxypiperidine-4-acetic acid methyl ester hydrochloride (0.105 g), substantially the same procedure as in Working Example 1 was followed to afford 0.125 g of a colorless amorphous solid product.

$^1$H-NMR(CDCl$_3$) δ: 1.35–1.84(6H,m), 2.47(2H,d), 2.65–2.85(1H,m), 2.95–3.28(2H,m), 3.35–3.78(7H,m), 3.62(3H,s), 3.73(3H,s), 3.90(3H,s), 4.22–4.40(2H,m), 4.52(1H,dd), 4.84(1H,dd), 6.13(1H,d), 6.62(1H,m), 6.95–7.43(5H,m)

Working Example 38

(3R,5S)-7-Chloro-1-(3-hydroxy-2-hydroxymethyl-2-methylpropyl)-1,2,3,5-tetrahydro-5-(2,3-dimethoxyphenyl)-3-(1H(or 3H)-tetrazol-5-yl)methyl-4,1-benzoxazepin-2-one

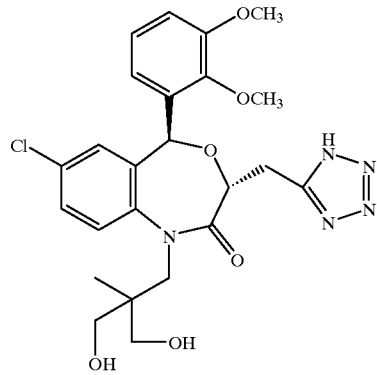

(1) To a solution of the compound produced in Working Example 20-(3) (0.5 g), ammonium chloride (0.25 g) and triethylamine (0.17 g) in dimethylformamide (5 ml) were added diethyl cyanophosphonate (0.21 g) and triethylamine (0.17 g). The mixture was stirred at room temperature for 30 minutes, to which was added ethyl acetate (50 ml). The mixture was washed with water, which was then dried over anhydrous sodium sulfate, followed by distilling off the solvent. The residue was purified by silica gel column chromatography (eluents: ethyl acetate) to give 0.52 g of an amide compound as amorphous solid.

(2) To a solution of dimethylformamide (41 mg) in acetonitrile (1.5 ml) was added oxalyl chloride (65 mg) at 0° C. The mixture was stirred for 10 minutes, to which were added a solution of the compound produced in (1) (0.25 g) in acetonitrile (1.5 ml) and pyridine (82 mg). The mixture was stirred at 0° C. for 10 minutes. To the reaction mixture was added ethyl acetate (50 ml). The mixture was washed with water and dried over anhydrous sodium sulfate, followed by distilling off the solvent. The residue was purified by silica gel column chromatography [eluents: hexane-ethyl acetate (2:1)] to give 0.31 g of a nitrile compound.

(3) A solution of the compound produced in (2) (1.0 g) in toluene (15 ml) was subjected to substantially the same procedure as in Working Example 7-(3), using trimethylsilyl azide (0.43 g) and dibutyltin (IV) oxide (45 mg) to give (3R,5S)-7-chloro-1-(2,2,5-trimethyl-1,3-dioxan-5-ylmethyl)-5-(2,3-dimethoxyphenyl)-1,2,3,5-tetrahydro-3-(tetrazol-5-yl)methyl-4,1-benzoxazepin-2-one (1.03 g) as a colorless amorphous solid product.

(4) To a solution of the compound produced in (3) (1.0 g) in acetone (10 ml) were added p-toluenesulfonic acid monohydrate (50 mg) and water (1 ml). The mixture was stirred at 60° C. overnight. To the reaction mixture was added water (50 ml), which was extracted with ethyl acetate. The organic layer was dried over anhydrous sodium sulfate. The solvent was distilled off, and the residue was purified by silica gel column chromatography [eluents: ethyl acetate-methanol (20:1)] to give 0.87 g of a colorless amorphous solid product.

$^1$H-NMR(CDCl$_3$) δ: 0.69(3H,s), 3.45(1H,dd,J=4.4, 14.4 Hz), 3.56–3.75(5H,m), 3.62(3H,s), 3.90(3H,s), 4.29(1H,dd, J=4.4, 8.8 Hz), 4.63(1H,d,J=15.2 Hz), 6.18(1H,s), 6.67(1H, d,J=2.2 Hz), 7.05–7.43(5H,m)

Working Example 39

(3R,5S)-1-(3-Acetoxy-2-acetoxymethyl-2-methylpropyl)-7-chloro-1,2,3,5-tetrahydro-5-(2,3-dimethoxyphenyl)-3-(1H(or 3H)-tetrazol-5-yl)-4,1-benzoxazepin-2-one

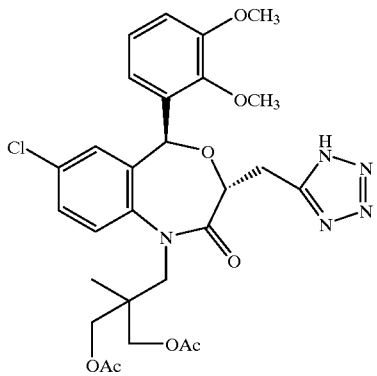

To a solution of the compound produced in Working Example 38 (0.77 g) in pyridine (7 ml) were added acetic anhydride (0.335 g) and dimethylaminopyridine (40 mg). The mixture was stirred at room temperature for 30 minutes, to which was added ethyl acetate (50 ml). The mixture was washed with 1N HCl and water, which was then dried over anhydrous sodium sulfate, followed by distilling off the solvent. The residue was washed with ethyl ether-hexane (1:1), which was filtrated to collect 0.80 g of a colorless amorphous solid product.

$^1$H-NMR(CDCl$_3$) δ: 0.98(3H,s), 2.03,2.04(each 3H,s), 3.40(1H,dd,J=5.1, 15.8 Hz), 3.55–3.67(2H,m), 3.65(3H,s), 3.82–3.91(2H,m), 3.89(3H,s), 4.04(1H,d,J=11.6 Hz), 4.18(1H,d,J=11.2 Hz), 4.30(1H,dd,J=5.2,6.6 Hz), 4.66(1H,d,J=14.6 Hz), 6.27(1H,s), 6.69(1H,d,J=2.2 Hz), 6.95–7.42(5H,m)

Working Example 40

(3R,5S)-N-[2-(Pyrrolidin-1-yl)ethyl]-7-chloro-1-(3-hydroxy-2-hydroxymethyl-3-methylpropyl)-5-(2,3-dimethoxyphenyl)-2-oxo-1,2,3,5-tetrahydro-4,1-benzoxazepine-3-acetamide

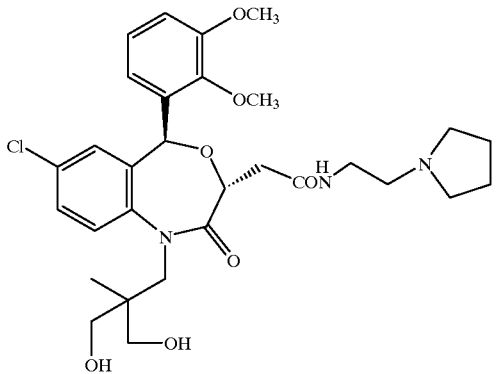

(1) To a solution of the compound produced in Working Example 20-(3) (0.5 g) and diethyl cyanophosphonate (54 mg) in dimethylformamide (1.5 ml) was added 1-(2-aminoethyl)pyrrolidine (0.16 g). The mixture was stirred at room temperature for 30 minutes, to which was added ethyl acetate (50 ml). The mixture was washed with water and dried, followed by distilling off the solvent. The residue was purified by silica gel column chromatography [eluents: ethyl acetate-methanol-triethylamine (10:1:0.1) to give (3R,5S)-N-[2-(pyridin-1-yl)ethyl]-7-chloro-1-(2,2,5-trimethyl-1,3-dioxan-5-ylmethyl)-5-(2,3-dimethoxyphenyl)-2-oxo-1,2,3,5-tetrahydro-4,1-benzoxazepine-3-acetamide (0.19 g) as a colorless amorphous solid product.

(2) To a solution of the compound produced in (1) (0.19 g) in tetrahydrofuran (2 ml) was added conc. HCl (1 ml). The mixture was stirred at 60° C. for 30 minutes, to which was added water (50 ml), followed by neutralizing with 1N NaOH. The resultant was extracted with ethyl acetate, washed with water and dried, followed by distilling off the solvent. The residue was purified silica gel column chromatography (eluents: ethyl acetate-methanol-triethylamine (2:1:0.1) to give 97 mg of a colorless amorphous solid product.

$^1$H-NMR(CDCl$_3$) δ: 0.62(3H,s), 1.75–1.80(4H,m), 2.50–2.72(7H,m), 2.87(1H,dd,J=7.0,14.2 Hz), 3.31–3.76 (7H,m), 3.59(3H,s), 3.89(3H,s), 4.45(1H,t),J=6.4 Hz), 4.82 (1H,d,J=15.0 Hz), 6.12(1H,s), 6.35–6.50(1H,br), 6.62(1H, s), 6.99–7.37(5H,m)

Working Example 41

(3R,5S)-N-Methylsulfonyl-1-(3-acetoxy-2,2-dimethylpropyl)-7-chloro-5-(2,3-dimethoxyphenyl)-2-oxo-1,2,3,5-tetrahydro-4,1-benzoxazepine-3-acetamide

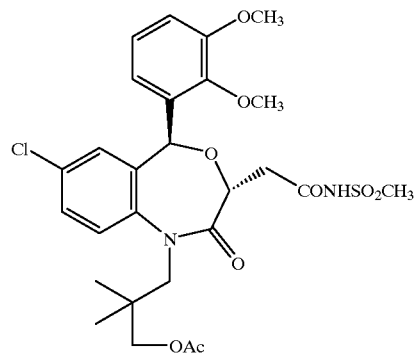

The compound produced in Working Example 19 (1.2 g) was subjected to substantially the same procedure as in Working Example 39 to give 1.01 g of a colorless crystalline product, m.p.108–112° C.

| Elemental Analysis for $C_{27}H_{33}ClN_2O_9S \cdot 1.5H_2O$: | |
|---|---|
| Calcd.: | C, 51.96; H, 5.81; N, 4.49 |
| Found: | C, 52.01; H, 5.82; N, 4.30 |

Working Example 42

(3R,5S)-1-(3-Acetoxy-2,2-dimethylpropyl)-7-chloro-5-(2,3-dimethoxyphenyl)-1,2,3,5-tetrahydro-3-[1H (or 3H)tetrazol-5-yl]methyl-4,1-benzoxazepin-2-one

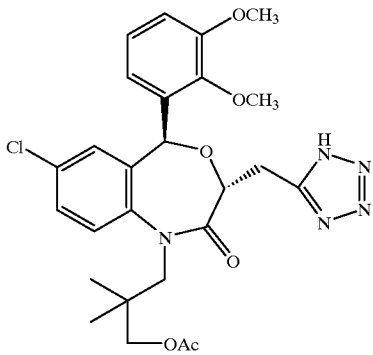

The compound produced in Working Example 11 (80 mg) was subjected to substantially the same procedure as in Working Example 39 to give 25 mg of a colorless amorphous solid product.

$^1$H-NMR(CDCl$_3$) δ: 0.97(3H,s), 0.99(3H,s), 2.05(3H,s), 3.3–3.8(4H,m), 3.65(3H,s), 3.89(3H,s), 4.05(1H,d), 4.28 (1H,dd), 4.62(1H,d), 6.27(1H,s), 6.68(1H,d), 6.9–7.4(5H,m)

Formulation Examples

A therapeutic agent of hyperlipemia containing, as its effective component, the compound (1) or a salt thereof of this invention can be formulated in accordance with, for example, the following prescriptions.

1. Capsules

| | |
|---|---|
| (1) N-[(3R,5S)-7-chloro-5-(2,3-dimethoxyphenyl)-1-neopentyl-2-oxo-1,2,3,5-tetrahydro-4,1-benzoxazepine-3-acetyl]piperidine-4-acetic acid | 10 mg |
| (2) Lactose | 90 mg |
| (3) Microcrystalline cellulose | 70 mg |
| (4) Magnesium stearate | 10 mg |
| 1 capsule | 180 mg |

(1), (2) and (3) and one half of (4) were blended and the mixture was granulated, to which was added the balance of (4). The mixture was filled in a gelatin capsule.

2. Tablets

| | |
|---|---|
| (1) N-[(3R,5S)-7-chloro-5-(2,3-dimethoxyphenyl)-1-neopentyl-2-oxo-1,2,3,5-tetrahydro-4,1-benzoxazepine-3-acetyl]piperidine-4-acetic acid | 10 mg |
| (2) Lactose | 35 mg |
| (3) Corn starch | 150 mg |
| (4) Microcrystalline cellulose | 30 mg |
| (5) Magnesium stearate | 5 mg |
| One tablet | 230 mg |

(1), (2), (3), two third of (4) and one half of (5) were blended and the mixture was granulated, to which were added the balance of (4) and (5). The mixture was subjected to compression-molding to provide tablets.

3. Injections

| | |
|---|---|
| (1) N-[(3R,5S)-7-Chloro-5-(2,3-dimethoxyphenyl)-1-neopentyl-2-oxo-1,2,3,5-tetrahydro-4,1-benzoxazepine-3-acetyl]piperidine-4-acetic acid | 10 mg |
| (2) Inositol | 100 mg |
| (3) Benzyl alcohol | 20 mg |
| One ampoule | 130 mg |

(1), (2) and (3) were dissolved in distilled water for injection to make the whole volume 2 ml, which was put in an ampoule, and the ampoule was sealed. All the processes were conducted under sterilized conditions.

Experimental Example 1

Squalene Synthetase Inhibitory Activity Assay Method

The squalene synthetase inhibitory activity was assayed as follows with the enzyme solutions prepared in accordance with the method described below.

More specifically, an enzyme solution (protein content 0.8 μg) prepared in accordance with the method described below was added to a solution (total volume 50 μl)) containing 5 μM [1-$^3$H] farnesyl pyrophosphate (specific activity 25 μCi/mole), 1 mM NADPH (nicotinamide adenine dinucleotide phosphate of reduced type), 5 mM MgCl$_2$, 6 mM glutathione, a 100 mM buffer solution of potassium phosphate (pH 7.4) and a test drug (used as an aqueous solution or a DMSO solution), then the reaction was allowed to proceed at 37° C. for 45 minutes. To the reaction mixture was added 150 μl of a mixture of chloroform and methanol (1:2) to suspend the reaction, followed by adding 50 μl of chloroform and 50 μl of a 3N solution of sodium hydroxide. 50 μl of the chloroform layer (lower layer) containing the reaction mixture having squalene as the principal component and 3 ml of toluene-based liquid scintillator were mixed, and its radioactivity was determined by means of a liquid scintillation counter.

The squalene synthetase inhibitory activity was expressed in terms of the concentration inhibiting by 50% the radioactivity taken into the chloroform layer (IC$_{50}$, molar concentration (M)), as shown in Table 7. Preparation of human-derived enzyme Human hepatic carcinoma cells HepG2 (about 1×10$^9$ cells) obtained by incubation on a Dulbecco-modified Eagle's medium (37° C. in the presence of 5% CO$_2$) containing 10% fetal bovine serum were suspended in 10 ml of an ice-cooled buffer solution [100 mM potassium phosphate buffer (pH 7.4), 30 mM nicotinamide and 2.5 mM MgCl$_2$]. The cells were crashed by means of ultrasonication (for 30 seconds, twice). The sonicate thus obtained was subjected to centrifugation for 20 minutes (4° C.) with 10000×g. The supernatant layer was subjected to further centrifugation for 90 minutes (4° C.) with 105000×g. The sediment was then suspended in an ice-cooled 100 mM potassium phosphate buffer (pH 7.4), which was again subjected to centrifugation for 90 minutes (4° C.) with 105000×g. This fraction was suspended in an ice-cooled 100 mM potassium phosphate buffer solution (pH 7.4) (about 4 mg/ml protein concentration). This suspension was used as the enzyme solution.

TABLE 7

| Compound No. | Inhibitory Activity (IC$_{50}$, $10^{-9}$M) |
|---|---|
| 4–2 | 22 |
| 4–8 | 11 |
| 4–9 | 11 |
| 4–10 | 11 |
| 4–12 | 11 |
| 4–15 | 19 |
| 4–18 | 18 |
| 4–19 | 18 |
| 4–20 | 17 |
| 4–21 | 11 |
| 4–24 | 14 |
| 4–26 | 15 |
| 4–29 | 15 |
| 4–30 | 12 |
| 4–31 | 20 |
| 7 | 11 |
| 8 | 12 |
| 9 | 9.5 |
| 13–2 | 18 |
| 17–1 | 13 |
| 17–2 | 9.3 |
| 17–3 | 11 |
| 17–4 | 9.3 |
| 18 | 15 |
| 19 | 32 |
| 20 | 48 |
| 21 | 26 |
| 22 | 8.5 |
| 23 | 12 |
| 24 | 17 |
| 25 | 29 |
| 27 | 20 |

As is clear from the above results, the compounds of this invention have an excellent squalene synthetase inhibitory activity.

Experimental Example 2

Assay of Cholesterogenesis in the Liver

Cholesterol biosynthesis in the liver of a rat was assayed as follows. Six-week old Wistar fatty rats were given orally a test compound [Compound 4-2 (suspended in a 0.5% methyl cellulose solution)], while the control group was orally given only a 0.5% methyl cellulose solution. One hour later, sodium acetate labelled with radioisotope $^{14}$C (manufactured by Amasham) was given intravenously at the tail (10 μCi/0.3 ml physiological saline/rat). One hour layer, rats were sacrificed by decapitation, and 1.5 g of the first lobe of the liver was removed, which was saponified by immersing in 3.9 ml of an alkaline ethanol solution (KOH:EtOH=1:2) at 100° C. for two hours, followed by extraction with 5 ml each portion of petroleum ether three times. The extract solution was dried, which was dissolved in 3 ml of ethanol:acetone (1:1). To the solution was added 2 ml of a 0.5% digitonin-ethanol solution. The mixture was left standing for one hour. Resulting precipitates were collected as total sterol, and the radioactivity was measured by means of a liquid scintillation counter. The results are shown below.

| Amount given | Cholesterogenesis inhibitory rate (%) |
|---|---|
| 0.6 mg/kg | 80.1% |
| 2.0 mg/kg | 90.4% |

As shown in the above results, the compound of this invention performs an excellent effect of inhibiting the cholesterogenesis by 80% or more.

Industrial Applicability

The compounds of this invention have a squalene synthetase inhibitory activity, a cholesterol lowering activity and a triglyceride lowering activity, and are useful as a prophylactic and therapeutic agent of hyperlipemia as an agent of lowering lipids, and also useful for prophylaxis and therapy of, among other, arteriosclerosis.

What is claimed is:

1. A compound selected from the group consisting of (i) (3R,5S)-7-Chloro-5-(2,3-dimethoxyphenyl)-1-(3-hydroxy-2,2-dimethylpropyl)-1,2,3,5-tetrahydro-3-[1H (or 3H)-tetrazol-5-yl]methyl-4,1-benzoxazepin-2-one, (ii) (3R,5S)-1-(3-Acetoxy-2,2-dimethylpropyl)-7-chloro-5-(2,3-dimethoxyphenyl)-1,2,3,5-tetrahydro-3-[1H (or 3H)-tetrazol-5-yl]methyl-4,1-benzoxazepin-2-one, (iii) (3R,5S)-N-methylsulfonyl-7-chloro-5-(2,3-dimethoxylphenyl)-1-(3-hydroxy-2,2-dimethylpropyl)-2-oxo-1,2,3,5-tetrahydro-4,1-benzoxazepine-3-acetamide, (iv) (3R,5S)-N-methylsulfonyl-1-(3-acetoxy-2,2-dimethylpropyl)-7-chloro-5-(2,3-dimethoxyphenyl)-2-oxo-1,2,3,5-tetrahydro-4,1-benzoxazepine-3-acetamide, (v) N-[(3R,5S)-7-chloro-5-(2,3-dimethoxyphenyl)-1-(3-hydroxy-2,2-dimethylpropyl)-2-oxo-1,2,3,5-tetrahydro-4,1-benzoxazepine-3-acetyl]piperdine-4-acetic acid, (vi) N-[(3R,5S)-1-(3-Acetoxy-2,2-dimethylpropyl)-7-chloro-5-(2,3-dimethoxylphenyl)-2-oxo-1,2,3,5-tetrahydro-4,1-benzoxazepine-3-acetyl]piperdine-4-acetic acid, (vii) N-[(3R,5S)-7-chloro-5-(2,3-dimethoxyphenyl)-1-(3-hydroxy-2,2-dimethylpropyl)-2-oxo-1,2,3,5-tetrahydro-4,1-benzoxazepine-3-acetyl]piperidine-4-carboxylic acid, and (viii) (3R,5S)-7-chloro-5-(2,3-dimethoxyphenyl)-1-(3-hydroxy-2,2-dimethylpropyl)-2-oxo-N-[2-(pyrrolidin-1-yl)ethyl]-1,2,3,5-tetrahydro-4,1-benzoxazepine-3-acetamide, or a salt thereof.

2. A composition comprising a compound as claimed in claim 1 and a pharmaceutically acceptable carrier.

3. A method for preparation of pharmaceutical composition comprising admixing a compound as described in claim 1 with a pharmaceutically acceptable carrier.

4. A method for inhibiting squalene synthetase for prophylaxis or therapy of hyperlipidaemia and renal diseases in a mammal, comprising administering an effective amount of a compound as claimed in claim 1 to said mammal.

5. A method for lowering the level of triglyceride in a mammal comprising administering an effective amount of a compound as claimed in claim 1 to said mammal.

6. A method for lowering the lipid-level in a mammal comprising administering an effective amount of a compound as claimed in claim 1 to said mammal.

7. A method for prophylaxis or therapy of hyperlipidaemia or coronary sclerosis in a mammal comprising administering an effective amount of a compound as claimed in claim 1 to said mammal.

* * * * *